United States Patent
Hynes et al.

(10) Patent No.: US 12,295,623 B1
(45) Date of Patent: May 13, 2025

(54) SURGICAL AND STABILIZATION TECHNIQUES FOR TREATMENT OF SACROILIAC JOINTS

(71) Applicant: EMPLASE Medical Technologies, LLC, Cordova, TN (US)

(72) Inventors: Richard A. Hynes, Melbourne, FL (US); Matthew M. Morrison, Cordova, TN (US)

(73) Assignee: EMPLASE MEDICAL TECHNOLOGIES, LLC, Cordova, TN (US)

( * ) Notice: Subject to any disclaimer, the term of this patent is extended or adjusted under 35 U.S.C. 154(b) by 0 days.

(21) Appl. No.: 18/740,176

(22) Filed: Jun. 11, 2024

Related U.S. Application Data

(60) Provisional application No. 63/563,077, filed on Mar. 8, 2024.

(51) Int. Cl.
*A61B 17/70* (2006.01)
*A61F 2/30* (2006.01)

(52) U.S. Cl.
CPC ...... *A61B 17/7055* (2013.01); *A61B 17/7079* (2013.01); *A61F 2002/30995* (2013.01)

(58) Field of Classification Search
CPC ............. A61B 17/7055; A61B 17/7079; A61F 2002/30995
USPC ...................... 606/246–249; 623/17.11–17.16
See application file for complete search history.

(56) References Cited

U.S. PATENT DOCUMENTS

| | | |
|---|---|---|
| 8,221,428 B2 | 7/2012 | Trieu |
| 8,551,171 B2 | 10/2013 | Johnson et al. |
| D742,517 S | 11/2015 | Schifano et al. |
| 9,271,758 B2 | 3/2016 | Marik et al. |
| 9,358,057 B1 | 6/2016 | Whipple et al. |
| 9,452,065 B1 | 9/2016 | Lawson |

(Continued)

FOREIGN PATENT DOCUMENTS

| | | |
|---|---|---|
| EP | 2869775 | 4/2018 |
| WO | 2011/056690 | 5/2011 |

(Continued)

OTHER PUBLICATIONS

Alderink, Gordon J.; The Sacroiliac Joint: Review of Anatomy, Mechanics, and Function; Journal of Orthopaedic & Sports Physical Therapy®; [accessed Jan. 12, 2024]; Feb. 1991.

(Continued)

*Primary Examiner* — Eduardo C Robert
*Assistant Examiner* — Tara Rose E Carter

(57) ABSTRACT

A method for facilitating stabilization of a sacroiliac joint is provided. The method includes surgical and stabilization techniques for implanting bone anchors or fasteners such as a first bone screw, a second bone screw, and third bone screw in a pelvis traversing portions of a coxal bone and a sacrum, and extending through or adjacent at least a portion of a corresponding sacroiliac joint. The bone anchors or fasteners such as the first bone screw, the second bone screw, and the third bone screw can be inserted at different angles and locations to form a lattice structure that serves in securing the position of a coxal bone and a sacrum relative to one another to facilitate stabilization across a corresponding sacroiliac joint.

23 Claims, 30 Drawing Sheets
(7 of 30 Drawing Sheet(s) Filed in Color)

(56) References Cited

U.S. PATENT DOCUMENTS

| | | |
|---|---|---|
| 9,474,624 B1 | 10/2016 | Ahn |
| D783,821 S | 4/2017 | Folsom et al. |
| 9,700,356 B2 | 7/2017 | Donner et al. |
| 9,717,538 B2 | 8/2017 | Chin et al. |
| 9,826,986 B2 | 11/2017 | Donner et al. |
| 9,861,375 B2 | 1/2018 | Assell et al. |
| 9,895,176 B2 | 2/2018 | Vestgaarden |
| D816,843 S | 5/2018 | Lewis |
| 10,219,841 B1 | 3/2019 | Compton et al. |
| D847,339 S | 4/2019 | Abbasi |
| 10,314,710 B2 | 6/2019 | Donner et al. |
| 10,335,197 B2 | 7/2019 | Donner et al. |
| 10,335,216 B2 | 7/2019 | Mari et al. |
| D857,897 S | 8/2019 | Loftus |
| D857,898 S | 8/2019 | Loftus |
| 10,383,664 B2 | 8/2019 | Donner et al. |
| 10,426,539 B2 | 10/2019 | Schifano et al. |
| 10,492,688 B2 | 12/2019 | Donner et al. |
| D879,295 S | 3/2020 | Abbasi |
| 10,588,750 B2 | 3/2020 | Souza et al. |
| 10,596,003 B2 | 3/2020 | Donner et al. |
| 10,596,004 B2 | 3/2020 | Donner et al. |
| 10,610,244 B2 | 4/2020 | Rindal et al. |
| 10,631,905 B2 | 4/2020 | Asfora et al. |
| 10,646,236 B2 | 5/2020 | Donner et al. |
| 10,675,094 B2 | 6/2020 | Crawford et al. |
| 10,722,369 B2 | 7/2020 | Mayer et al. |
| 10,736,752 B1 | 8/2020 | Schifano et al. |
| 10,779,958 B2 | 9/2020 | Lins |
| 10,813,679 B2 | 10/2020 | Lanois et al. |
| 10,842,511 B2 | 11/2020 | Patel et al. |
| 10,905,472 B2 | 2/2021 | Mari et al. |
| 10,925,653 B2 | 2/2021 | Mari |
| 10,932,838 B2 | 3/2021 | Mehl et al. |
| 10,952,749 B2 | 3/2021 | Abbasi |
| 10,987,144 B2 | 4/2021 | Asfora |
| 10,993,754 B2 | 5/2021 | Kuntz et al. |
| 2011/0184284 A1 | 7/2011 | McKay |
| 2012/0191191 A1* | 7/2012 | Trieu .................. A61B 17/864 623/17.11 |
| 2015/0112444 A1 | 4/2015 | Aksu |
| 2015/0157377 A1 | 6/2015 | Pham et al. |
| 2015/0182268 A1* | 7/2015 | Donner .............. A61B 17/8872 606/291 |
| 2016/0310197 A1 | 10/2016 | Black et al. |
| 2017/0296346 A1 | 10/2017 | Assell et al. |
| 2018/0185078 A1 | 7/2018 | Na et al. |
| 2018/0325570 A1 | 11/2018 | Kuntz et al. |
| 2019/0209011 A1 | 7/2019 | Donner et al. |
| 2019/0381285 A1 | 12/2019 | Althoff et al. |
| 2019/0388131 A1 | 12/2019 | Mehl et al. |
| 2020/0060733 A1 | 2/2020 | Compton et al. |
| 2020/0121375 A1 | 4/2020 | Schifano et al. |
| 2020/0281729 A1 | 9/2020 | Schifano et al. |
| 2020/0375750 A1 | 12/2020 | Abbasi et al. |
| 2021/0015630 A1 | 1/2021 | Wall |
| 2021/0100658 A1 | 4/2021 | LaNeve et al. |
| 2021/0100661 A1 | 4/2021 | LaNeve et al. |
| 2021/0100662 A1 | 4/2021 | LaNeve et al. |

FOREIGN PATENT DOCUMENTS

| | | |
|---|---|---|
| WO | 2013/177355 | 11/2013 |
| WO | 2014/007953 | 1/2014 |
| WO | 2016/147080 | 9/2016 |
| WO | 2019/152737 | 8/2019 |

OTHER PUBLICATIONS

Beck et al.; A Retrospective Outcomes Study of 20 Sacroiliac Joint Fusion Patients; Cureus 7(4): e260; Apr. 2015.
Bell, Daniel J. et al.; Sacroiliac joint (AP oblique view); Radiopaedia; undated.
Biofusion Medical LLC; SI-Restore® Sacroiliac Joint Fixation System; Bone Screw or Internal Fixation Device; FDA U.S. Food & Drug Administration; Section 510(k) No. K200868; Apr. 2020.
Cabaj, Maciej et al.; Spinal instrumentation DERO system for the treatment of thoracic nd lumbar spine neoplasms. The preliminary report; System Dero: Rozwój Technik Operacy Jnego Leczenia Kregoslupa; undated.
Centene Corporation; Clinical Policy: Sacroiliac Joint Interventions for Pain Management; Reference No. CP.MP.166; Feb. 2020.
Centeno, Chris; SI Joint Fusion Surgery Side Effects: This is a Dumb Idea; Regennexx® Jul. 2015.
Chin, Kingsley R. et al.; 2-year CT scan follow up of posterior sacroiliac joint compression fixation; Abstract; LESSociety (Less Exposure Surgery Society); undated.
Chuang, Ching-Wei et al.; Diagnosis and interventional pain management options for sacroiliac joint pain; Tzu Chi Medical Journal 2019; 31(4): 207-210.
Clinical examination of the sacroiliac joint; The Sacroiliac Joint and Coccyx; Chapter 41; pp. 595-6090.e1; 2013.
Cohen, Steven et al.; Sacroiliac joint pain: A comprehensive review of epidemiology, diagnosis and treatment; ResearchGate; Expert Review of Neurotherapeutics; pp. 99-116; Jan. 2013.
Cohen, Steven P.; Sacroiliac Joint Pain: A Comprehensive Review of Anatomy, Diagnosis, and Treatment; Anesth Analg; 101:1440-53; 2005.
Cross III, William W. et al.; In Vitro Biomechanical Evaluation of a Novel, Minimally Invasive, Sacroiliac Joint Fixation Device; International Journal of Spine Surgery, vol. 12, No. 5, pp. 587-594; 2018.
Cusi, Manuel F.; Paradigm for assessment and treatment of SIJ mechanical dysfunction; Journal of Bodywork & Movement Therapies; pp. 152-161; 2010.
Delmonico, Kim; 510(K) Clearance for a 'Bowtie' SI Joint Fixation Device; Orthopedics This Week; https://ryortho.com/breaking/510k-clearance-for-a-bowtie-si-joint-fixation-device/; [accessed Jul. 30, 2024]; May 2024.
Forst, Stacy L. et al.; The Sacroiliac Joint: Anatomy, Physiology and Clinical Significance; Pain Physician; vol. 9; No. 1; pp. 61-68, ISSN 1533-3159; 2006.
Fortin, Joseph D. et al.; Three Pathways between the Sacroiliac Joint and Neural Structures; American Society of Neuroradiology; AJNR 20; pp. 1429-1434; Sep. 1999.
Globus Medical; SI-LOK™ Sacroiliac Joint Fixation System; Patient Information; undated.
Grechenig, Peter et al.; Relation of the lumbosacral trunk to the sacro-iliac joint; Scientific Reports; 2021.
Highsmith, Jason M.; Treatments for Sacroiliac Joint Dysfunction—There are many different non-surgical treatment options for SI joint dysfunction, such as sacroiliac bracing and medications; Spine Universe; https://www.spineuniverse.com/print/conditions/sacroiliac-joint-dysfunction/treatments-sacroiliac-joint-dysfunction; [accessed Apr. 7, 2021]; 2021.
Inspired Spine announces Trident™ SI Joint Screw System Secures FDA 510(k) Approval; https://finance.yahoo.com/news/inspired-spine-announces-trident-si-184 . . . [accessed May 4, 2021]; Jan. 2021.
Inspired Spine; Inspired Spine receives FDA clearance for Trident SI Joint Screw System; https://spinalnewsinternational.com/inspired-spine-receives-fda-clearanc . . . ; [accessed May 3, 2021]; Jan. 2021.
Inspired Spine; Inspired Spine receives FDA clearance for Trident SI Joint Screw System; https://spinalnewsinernational.com/inspired-spine-receives-fda-clearance-for-trident-si-joint-screw-system/; [accessed May 4, 2021]; Spinal News International; Jan. 2021.
Inspired Spine; Sacroiliac Joint Fusion Post Op Instructions; undated.
ISaF; Dero Spinal System—ISaF IlioSacral autogenic fusion; https://lfc.com.pl/produkt/isaf/?lang-en; [accessed May 4, 2021].
Kiapour, Ali; Biomechanics of the Sacroiliac Joint: Anatomy, Function, Biomechanics, Sexual Dimorphism, and Causes of Pain; International Journal of Spine Surgery, vol. 14, Supplement 1; pp. S3-S13; 2020.

(56) References Cited

OTHER PUBLICATIONS

Laslett, Mark; Clinical Perspective—Evidence-Based Diagnosis and Treatment of the Painful Sacroiliac Joint; The Journal of Manual & Manipulative Therapy, vol. 16, No. 3; pp. 144-152; undated.

Le Huec et al.; Instructional Lecture: Spine—A painful unknown: sacroiliac joint diagnosis and treatment; Efort Open Reviews; vol. 5, Oct. 2020.

Lee, Anderson et al.; Sacroiliitis: A Review on Anatomy, Diagnosis, and Treatment; Hindawi; Advances in Orthopedics, vol. 2022, Article ID 3283296; 2022.

Lee, David W.; Review of Current Evidence for Minimally Invasive Posterior Sacroiliac Joint Fusion; International Journal of Spine Surgery; May 2021.

Mayo Clinic; Sacroiliitis: Patient Care & Health Information > Diseases & Conditions; https://www.mayoclinic.org/diseases-conditions/sacroiliitis/diagnosis-treatment/drc-20350751; [accessed Apr. 7, 2021]; 2021.

Medacta International; M.U.S.T. SI Sacro-iliac Joint Screw System—A Complete System with Different Options; Brochure; undated.

Medical Designs; Sacroiliac Joint Fixation with Samba™ Screw System—Surgical Procedure Manual; 2012.

Neha, Bharti et al.; Effectiveness of Therapeutic Interventions in Sacroiliac Joint Dysfunction: A Systematic Review; International Journal of Physiotherapy and Research; 2016, vol. 4(3):1484-88; ISSN 2321-1822.

Omnia Medical; PsiF Posterior SI Fusion; Brochure; undated.

Orthofix; Firebird® SI—SI Fusion System; Operative Technique; Mar. 2020.

Orthofix; SambaScrew® SI Fixation System—Sacroiliac Joint Fixation; Operative Technique; Jun. 2020.

Orthostreams; 26 players in the SI joint market; https://orthostreams.com/2020/07/26-players-in-the-si-join-market/; [accessed May 4, 2021]; Tiger Ortho Consulting; 2020.

Patient Instructions: Sacroiliac (SI) Joint Fusion; undated.

Poilliot, Amelia J.; A Systematic Review of the Normal Sacroiliac Joint Anatomy and Adjacent Tissues for Pain Physicians; Pain Physician 2019; 22:E247-E274; ISSN 2150-1149; Jul./Aug. 2019.

Polly Jr., David W. et al.; Symptoms Related to Sacroiliac Joint Dysfunction; Spine Universe; https://www.spineuniverse.com/print/conditions/sacroiliac-joint-dysfunction/sacroiliac-joint-dysfunction-symptoms;I [accessed Apr. 7, 2021]; 2021.

Prati, Clement et al.; Novel insights into the anatomy and histopathology of the sacroiliac joint and correlations with imaging signs of sacroiliitis in case of axial spondyloarthritis; Frontiers in Physiology; pp. 01-11; May 2023.

Premera Blue Cross; Diagnosis and Treatment of Sacroiliac Joint Pain; Medical Policy—Jun. 1, 2023; Feb. 2021.

Raji, Oluwatodimu R. et al.; Transfixing the Sacroiliac Joint with the SiLO™ Graft—A Cadaver-Based Biomechanical Investigation; Aurora Pain Care; F220149_B; 2021.

Robotic SI Fuse; Medtronic Rialto SI Fusion Cage; https://www.roboticsifuse.com/eduction/medtronic-rialto-si-fusion-cage; [accessed May 4, 2021] 2021.

Sherman, Andrew L. et al.; Sacroiliac Joint Injury Treatment & Management; Medscape; https://emedicine.medscape.com/ article/96054-treatment#showall; [accessed Apr. 15, 2021]; Jan. 2019.

SI-Bone; Corporate Overview; May 2021.

SI-Bone; Instructions for Use—iFuse-TORQ™ Implant System; 501381 Rev. A; Release Date Mar. 2021.

SI-Bone; The Symptomatic SI Joint—Clinical Examination, Diagnosis and Treatment; 9228.062017; 2017.

SI-Bone; Your Journey to SI Joint Pain Relief; undated.

SI-Bone®; Sacroiliac (SI) Joint Diagnosis and Injections; iFuse Implant System—Minimally Invasive Sacroiliac Joint Surgery; 2018.

Signus Medizintechnik GmbH; DIANA®—Distraction-Interference-Arthrodesis with Neurovascular Anticipation; Product Information; Rev. 2015—Sep. 2002.

Simopoulos, Thomas T., MD; A Systematic Evaluation of Prevalence and Diagnostic Accuracy of Sacroiliac Joint Interventions; Pain Physician 2012; 15:E305-E344; ISSN 2150-1149; May/Jun. 2012.

SI-Technology, LLC; Si-Technology® Si-Desis® Screws; Smooth or threaded metallic bone fixation fastener; FOIA Request #2015-8275; Released by CDRH on Nov. 20, 2018; Section 510(k) No. K151462; Jul. 2015.

SI-Technology; Si-Technology® SI-Desis® Sacroiliac Joint Fusion Screw System—Surgical Technique Guide; MKG-20000 Rev. 01-Draft; Jul. 2015.

The Expresswire; MIS Sacroiliac Joint Fusion Market Size 2021-2026: Research Report by Key Companies, Future Trend, Pipeline Projects, Product, Application, Growth and Regional Forecasts; MarketWatch Press Release; https://www.marketwatch.com/press-release/mis-sacroiliac-joint-fusion...projects-product-application-growth-and-regional-forecasts-2021-02-15; [accessed Apr. 15, 2021] Feb. 2021.

Tristate Arthritis & Rheumatology; Types of Arthritis That Cause Sacroiliac Joint Pain and Their Symptoms . . .; https://www.tristatearthritis.com/arthritis/types-of-arthritis-that-cause-sacroiliac-joint-pain-and-their-symptoms/; [accessed Apr. 7, 2021]; 2021.

Tsoi, Carita et al.; Imaging of sacroiliitis: Current status, limitations and pitfalls; Quantitative Imaging in Medicine and Surgery, vol. 9, No. 2; pp. 318-335; Feb. 2019.

Vallejo, Ricardo et al.; Pulsed Radiofrequency Denervation for the Treatment of Sacroiliac Joint Syndrome; Pain Medicine, vol. 7, No. 5; pp. 429-434; 2006.

Vetalice, Julie A.; Inspired Spine Debuts Trident Sacroiliac Joint Fusion; Orthoworld Products, Spine Jul. 2020; https://www.orthoworld.com/inspired-spine-debuts-trident-sacroiliac-join . . . ; [accessed May 4, 2021].

Vleeming, A. et al.; The sacroiliac joint: an overview of its anatomy, function and potential clinical implications; Journal of Anatomy; pp. 537-567; 2012.

Washington State Health Care Authority; Sacroiliac joint fusion update: Draft Key Questions and Background; Jan. 2021.

Woods, Candace—Alevio, LLC; Alevio® completes the 500$^{th}$ case with SiCure™ Sacroiliac Fusion System; https://www.prweb.com/releases/2017/06/prweb14466134.html [accessed May 3, 2021]; PRWEB; Jun. 2017.

Xtant Medical; Silex® Sacroiliac Joint Fusion System—Sacroiliac compression and stability for rapid and solid joint fusion; Brochure FM-C-MRK-80(B); May 2020.

Zimmer Biomet; TriCor™ Sacroiliac Joint Fusion System—Surgical Technique Guide; 0437.1-GLBL-en-REV0417; 2017.

Zimmer Biomet; TriCor™ Sacroiliac Joint Fusion System Coding Reference Guide; 0010.3-US-en-REV1216; 2016.

\* cited by examiner

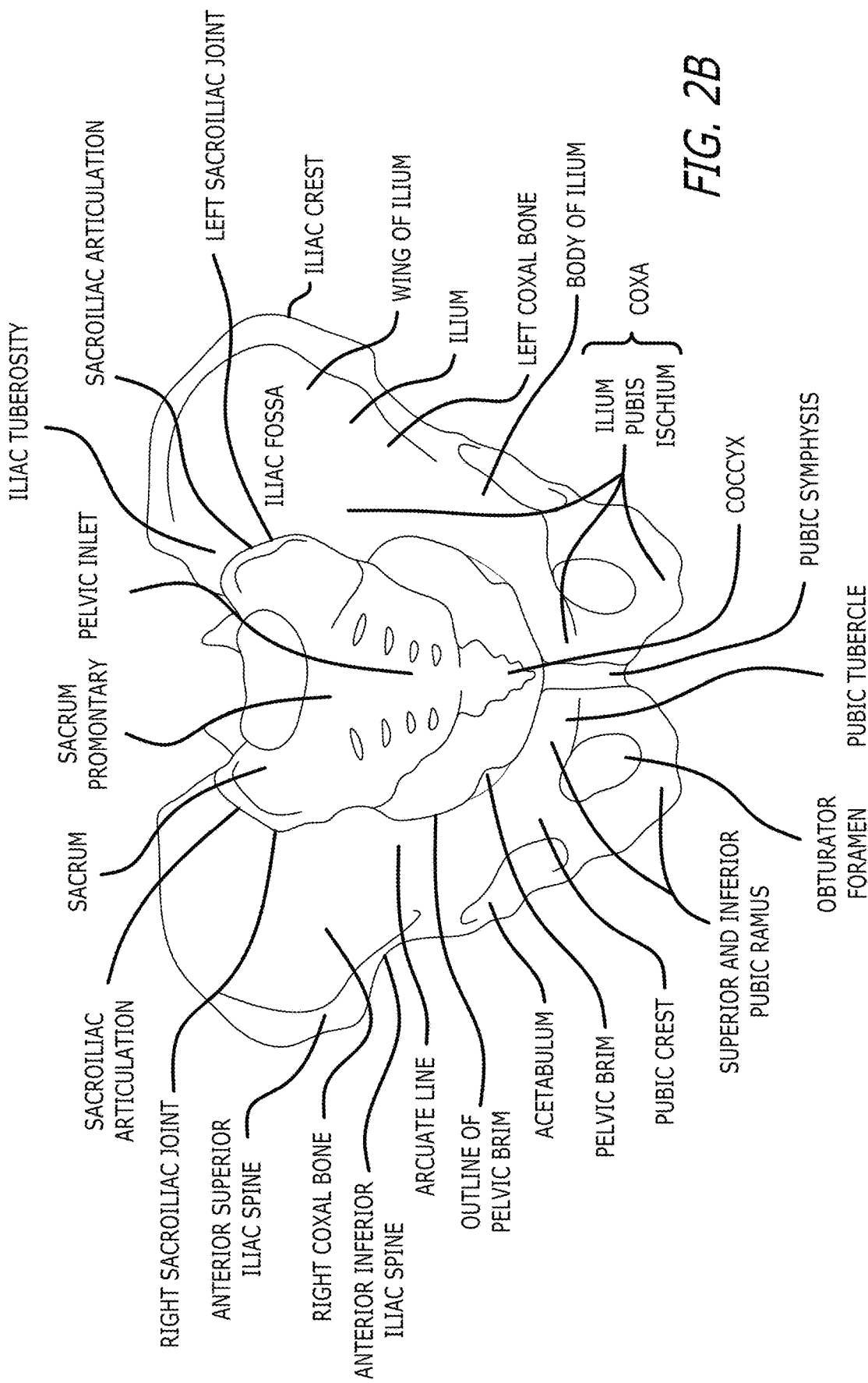

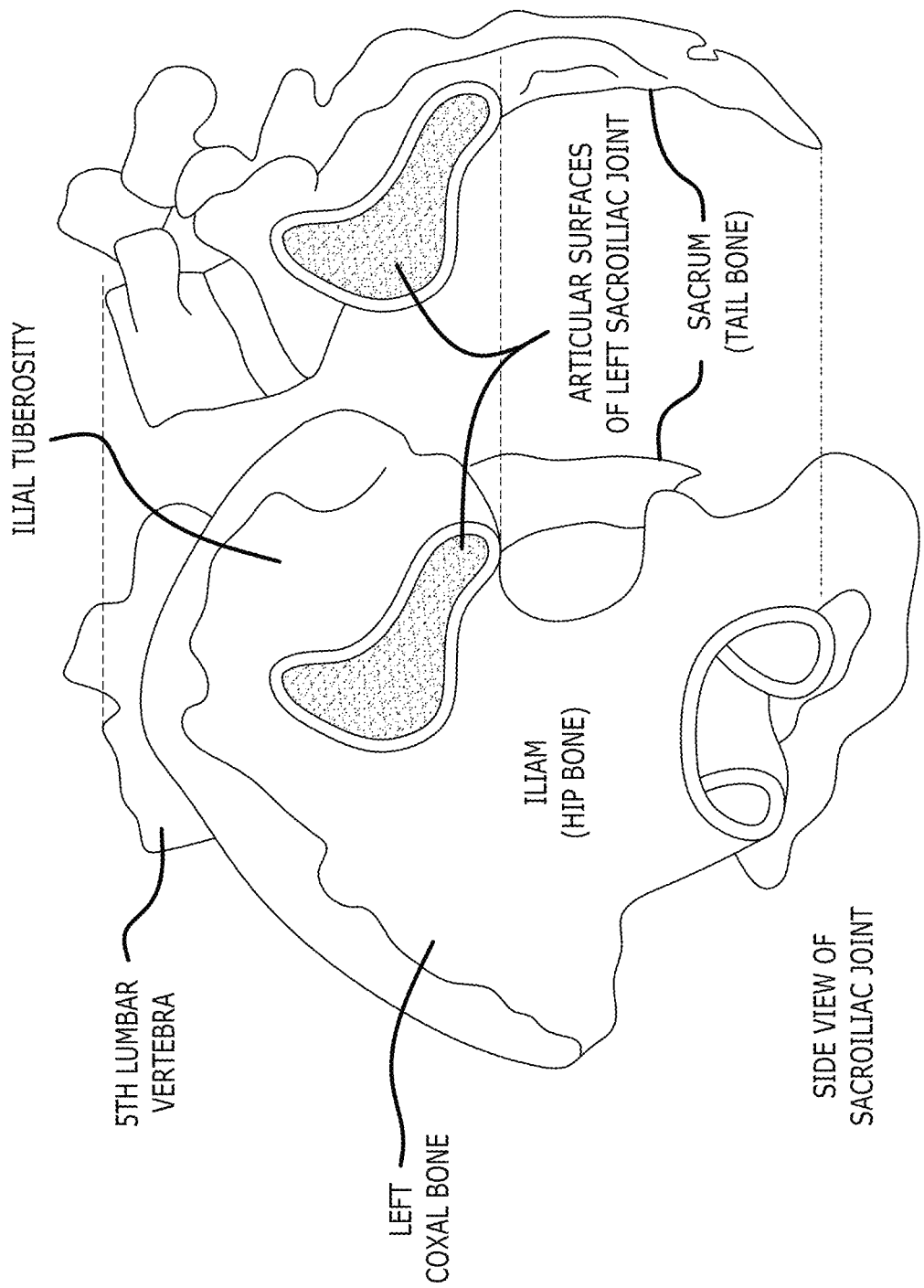

SURGICAL AND STABILIZATION TECHNIQUES FOR TREATMENT OF SACROILIAC JOINTS

The present application claims the benefit of Provisional Application No. 63/563,077, filed Mar. 8, 2024, all of which is incorporated by reference.

FIELD OF INVENTION

The present disclosure relates to methods for facilitating stabilization of a sacroiliac joint and includes surgical and stabilization techniques for implanting a first bone screw, a second bone screw, and third bone screw through a coxal bone, through or adjacent at least a portion of a corresponding sacroiliac joint, and into a sacrum, with the first bone screw, the second bone screw, and the third bone screw being inserted at different angles and locations to form a lattice structure that serves in securing the position of the coxal bone and the sacrum relative to one another to facilitate stabilization across the corresponding sacroiliac joint.

BACKGROUND

Sacroiliac joints of a pelvis of a human body are located between left and right sides of a sacrum and corresponding left and right coxal bones. The sacroiliac joints serve in transferring loads between a lumbar spine and lower extremities of the human body. Dysfunction of the sacroiliac joints can cause sacroiliitis, which is joint pain and inflammation resulting from such dysfunction of the sacroiliac joints. Such dysfunction can be caused by damage to nerves located adjacent the sacroiliac joints, and damage to joint capsules, cartilage, ligaments, and/or muscles associated with the sacroiliac joints. And articulation of the sacroiliac joints can exacerbate such joint pain and inflammation. Conventional surgical and conventional stabilization techniques typically use three (3) bone screws parallelly implanted posteriorly or posterolaterally through portions of iliac crests and/or portions of posterior gluteal surfaces adjacent the iliac crests, through the corresponding sacroiliac joints, and into the sacrum to hold the left or the right coxal bones in position relative to one another and constrain movement therebetween. However, the mechanical properties afforded by the parallel implantation of the three (3) bone screws, and the potentially poor strength of the sacral bone compared to the bone of the left and the right iliums and the corresponding modest sacral fixation of the conventional surgical and the conventional stabilization techniques are not ideal, and undesirable movement of the sacroiliac joint can still occur. Therefore, there is a need for surgical and stabilization techniques that can more effectively stabilize the sacroiliac joints to better resist movement thereof in multiple directions when under load to thereby inhibit joint pain and inflammation associated with the sacroiliac joints.

SUMMARY

The subject of the present disclosure relates to methods for facilitating stabilization of a sacroiliac joint and includes surgical and stabilization techniques for doing so.

In one aspect, the present disclosure provides a method for facilitating stabilization of a selected one of a right sacroiliac joint and a left sacroiliac joint of a pelvis of a patient, the method including providing an incision in one of a right portion and a left portion of a back and/or buttocks of the patient corresponding to the selected one of the right sacroiliac joint and the left sacroiliac joint; accessing a posterior portion of one of a right coxal bone and a left coxal bone of the patient corresponding to the selected one of the right sacroiliac joint and the left sacroiliac joint; preparing a first insertion hole through a first portion of the one of the right coxal bone and the left coxal bone, through or adjacent at least a portion of the one of the right sacroiliac joint and the left sacroiliac joint, and into one of a right side and a left side of a sacrum of the patient corresponding to the selected one of the right sacroiliac joint and the left sacroiliac joint; preparing a second insertion hole through a second portion of the one of the right coxal bone and the left coxal bone, through or adjacent at least a portion of the one of the right sacroiliac joint and the left sacroiliac joint, and into the one of the right side and the left side of the sacrum; preparing a third insertion hole through a third portion of the one of the right coxal bone and the left coxal bone, through or adjacent at least a portion of the one of the right sacroiliac joint and the left sacroiliac joint, and into the one of the right side and the left side of the sacrum; inserting a first bone anchor through and into the first insertion hole to interconnect the one of the right coxal bone and the left coxal bone, and the one of the right side and the left side of the sacrum; inserting a second bone anchor through and into the second insertion hole to interconnect the one of the right coxal bone and the left coxal bone, and the one of the right side and the left side of the sacrum; inserting a third bone anchor through and into the third insertion hole to interconnect the one of the right coxal bone and the left coxal bone, and the one of the right side and the left side of the sacrum; and forming a lattice construct by implantation of the first bone anchor, the second bone anchor, and the third bone anchor to constrain movement between the one of the right coxal bone and the left coxal bone, and the one of the right side and the left side of the sacrum to facilitate stabilization across the one of the right sacroiliac joint and the left sacroiliac joint; where the first bone anchor, the second bone anchor, and the third bone anchor each include a first end, an opposite second end, and a mid-longitudinal axis extending through the first end and the second end, and planes extending along each of the mid-longitudinal axis intersect with one another.

In another aspect, the present disclosure provides a method for facilitating stabilization of a selected one of a right sacroiliac joint and a left sacroiliac joint of a pelvis of a patient, the method including providing an incision in one of a right portion and a left portion of a back and/or buttocks of the patient corresponding to the selected one of the right sacroiliac joint and the left sacroiliac joint; accessing a posterior portion of one of a right coxal bone and a left coxal bone of the patient corresponding to the selected one of the right sacroiliac joint and the left sacroiliac joint; preparing a first insertion hole through a first portion of the one of the right coxal bone and the left coxal bone, through or adjacent at least a portion of the one of the right sacroiliac joint and the left sacroiliac joint, and into one of a right side and a left side of a sacrum of the patient corresponding to the selected one of the right sacroiliac joint and the left sacroiliac joint; preparing a second insertion hole through a second portion of the one of the right coxal bone and the left coxal bone, through or adjacent at least a portion of the one of the right sacroiliac joint and the left sacroiliac joint, and into the one of the right side and the left side of the sacrum; preparing a third insertion hole through a third portion of the one of the right coxal bone and the left coxal bone, through or adjacent at least a portion of the one of the right sacroiliac joint and the left sacroiliac joint, and into the one of the right side and the left side of the sacrum; inserting a first bone anchor through and into the first insertion hole to interconnect the one of the right coxal bone and the left coxal bone, and the one of the right side and the left side of the sacrum; inserting a second bone anchor through and into the second insertion hole to interconnect the one of the right coxal bone and the left coxal bone, and the one of the right side and the left side of the sacrum; inserting a third bone anchor through and into the third insertion hole to interconnect the one of the right coxal bone and the left coxal bone, and the one of the right side and the left side of the sacrum; and forming a lattice construct by implantation of the first bone anchor, the second bone anchor, and the third bone anchor to maintain the position of the one of the right coxal bone and the left coxal bone relative to the sacrum; where, after implantation thereof, the first bone anchor is angled at approximately 83 degrees+/−7 degrees relative to a coronal plane extending through the center of the pelvis, angled at approximately 0 degrees+/−3 degrees relative to an axial plane extending through the center of the pelvis, and angled at approximately 20 degrees+/−8 degrees relative to a sagittal plane extending through the center of the pelvis, the second bone anchor is angled at approximately 45 degrees+/−25 degrees relative to the coronal plane extending through the center of the pelvis, angled at approximately 35 degrees+/−25 degrees relative to the axial plane extending through the center of the pelvis, and angled at approximately 60 degrees+/−30 degrees relative to the sagittal plane extending through the center of the pelvis, and the third bone anchor is angled at approximately 40 degrees+/−7 degrees relative to the coronal plane extending through the center of the pelvis, angled at approximately 20 degrees+/−10 degrees relative to the axial plane extending through the center of the pelvis, and angled at approximately 35 degrees+/−25 degrees relative to the sagittal plane extending through the center of the pelvis.

In yet another aspect, the present disclosure provides a method for facilitating stabilization of a selected one of a right sacroiliac joint and a left sacroiliac joint of a pelvis of a patient, the method including providing an incision in one of a right portion and a left portion of a back and/or buttocks of the patient corresponding to the selected one of the right sacroiliac joint and the left sacroiliac joint; accessing a posterior portion of one of a right coxal bone and a left coxal bone of the patient corresponding to the selected one of the right sacroiliac joint and the left sacroiliac joint; preparing a first insertion hole through a first portion of the one of the right coxal bone and the left coxal bone, through or adjacent at least a portion of the one of the right sacroiliac joint and the left sacroiliac joint, and into one of a right side and a left side of a sacrum of the patient corresponding to the selected one of the right sacroiliac joint and the left sacroiliac joint; preparing a second insertion hole through a second portion of the one of the right coxal bone and the left coxal bone, through or adjacent at least a portion of the one of the right sacroiliac joint and the left sacroiliac joint, and into the one of the right side and the left side of the sacrum; preparing a third insertion hole through a third portion of the one of the right coxal bone and the left coxal bone, through or adjacent at least a portion of the one of the right sacroiliac joint and the left sacroiliac joint, and into the one of the right side and the left side of the sacrum; inserting a first bone anchor through and into the first insertion hole to interconnect the one of the right coxal bone and the left coxal bone, and the one of the right side and the left side of the sacrum at approximately 83 degrees+/−7 degrees relative to a coronal plane extending through the center of the pelvis, approximately 0 degrees+/−3 degrees relative to an axial plane extending through the center of the pelvis, and approximately 20 degrees+/−8 degrees relative to a sagittal plane extending through the center of the pelvis; inserting a second bone anchor through and into the second insertion hole to interconnect the one of the right coxal bone and the left coxal bone, and the one of the right side and the left side of the sacrum at approximately 45 degrees+/−25 degrees relative to the coronal plane extending through the center of the pelvis, approximately 35 degrees+/−25 degrees relative to the axial plane extending through the center of the pelvis, and at approximately 40 degrees+/−30 degrees relative to the sagittal plane extending through the center of the pelvis; inserting a third bone anchor through and into the third insertion hole to interconnect the one of the right coxal bone and the left coxal bone, and the one of the right side and the left side of the sacrum at approximately 60 degrees+/−7 degrees relative to the coronal plane extending through the center of the pelvis, approximately 40 degrees+/−10 degrees relative to the axial plane extending through the center of the pelvis, and at approximately 35 degrees+/−25 degrees relative to the sagittal plane extending through the center of the pelvis; and forming a lattice construct by implantation of the first bone anchor, the second bone anchor, and the third bone anchor to maintain the position of the one of the right coxal bone and the left coxal bone relative to the sacrum.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2B is a posterior representative view also depicting the pelvis of the human body depicting the coxal bones, the sacrum, and the coccyx, and illustrating the left sacroiliac joint and the right sacroiliac joint;

FIG. 4A is a left-side exploded (partially phantom) representative view of a left coxal bone and the sacrum that form the left sacroiliac joint;

DETAILED DESCRIPTION

Figure 1:
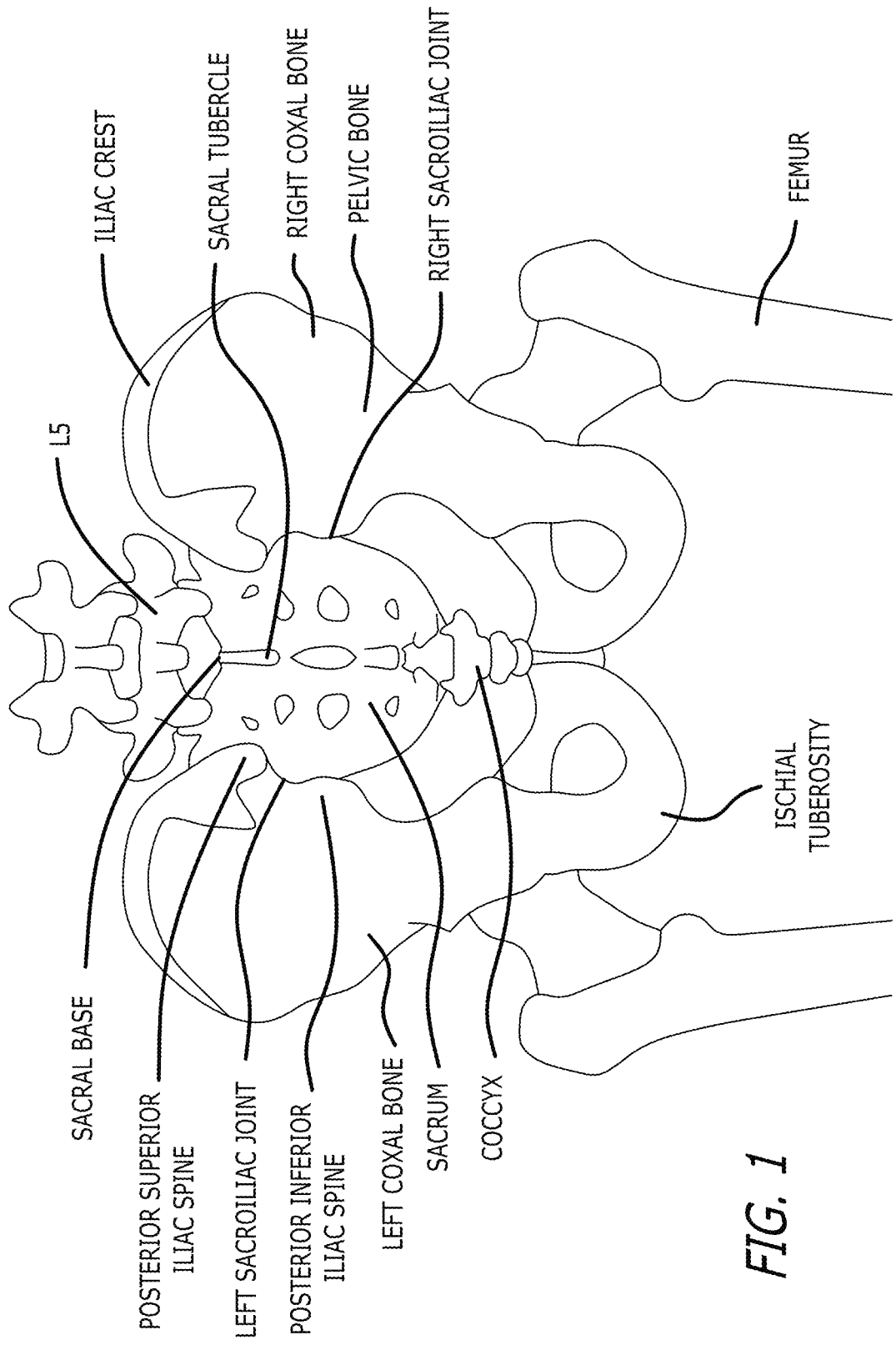
FIG. 1 is an anterior representative view illustrating a pelvic region depicting a pelvis, a portion of a left femur, a portion of a right femur, and portions of a lumber spine of a human body.
Figure 2A:
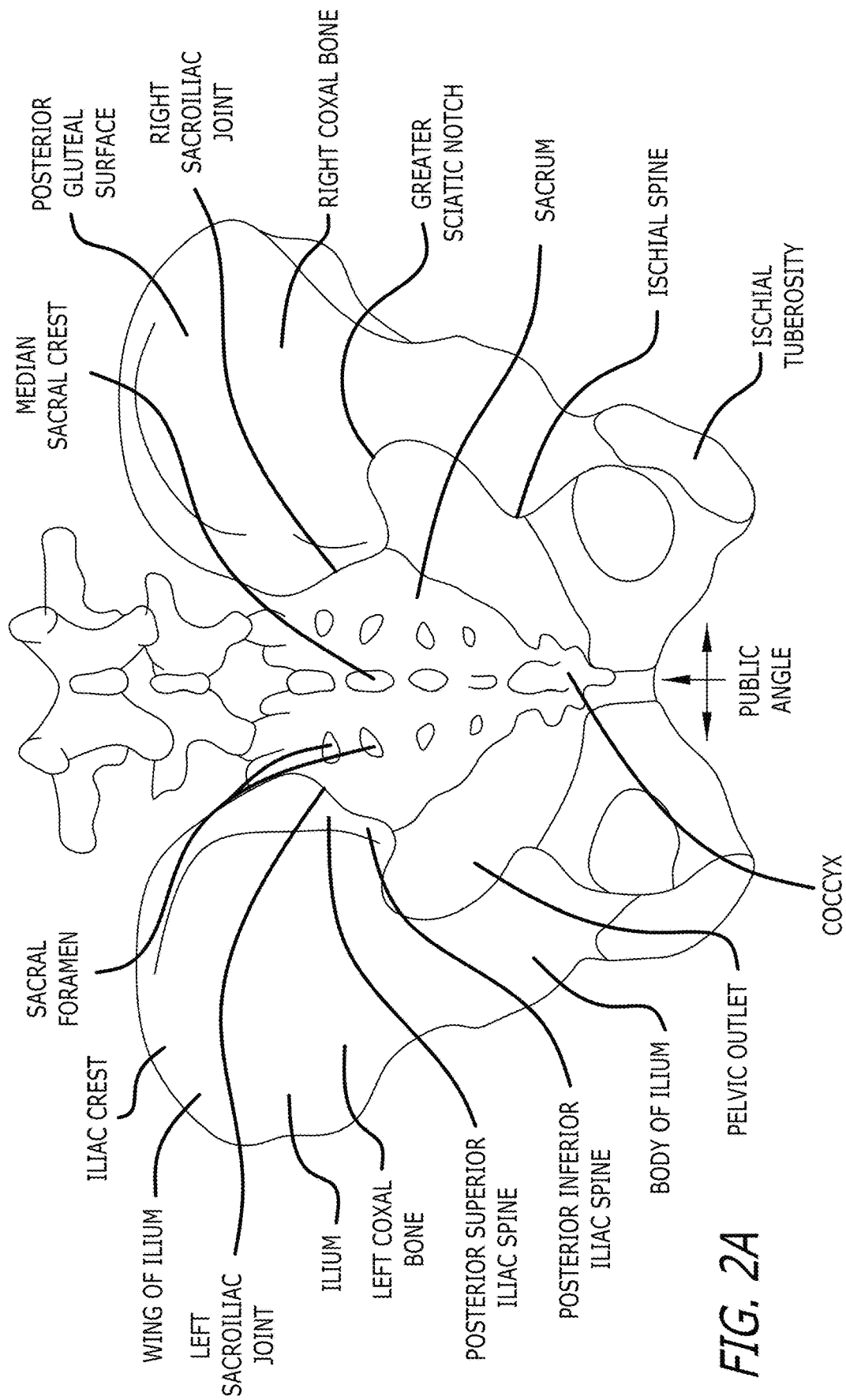
FIG. 2A is an anterior representative view illustrating the pelvis of the human body depicting coxal bones, a sacrum, and a coccyx, and illustrating a left sacroiliac joint and a right sacroiliac joint between the coxal bones and the sacrum.

In a human body, as depicted in FIG. 1, sacroiliac joints are located between left and right sides of a sacrum and corresponding left and right coxal bones of a pelvis. More specifically, as depicted in FIGS. 2A and 2B, left and right sacroiliac joints are formed between an ilium of each of the left and the right coxal bones, and corresponding portions of the left and the right sides of the sacrum. More specifically, the left and the right sides of the sacrum each include an auricular surface (FIGS. 3B, 4A, and 4B) of the left and the right sacroiliac joints, respectively, and the left and the right coxal bones (FIGS. 4A and 4B) each also include a corresponding auricular surface.

The iliums of the left and the right coxal bones, as depicted in FIGS. 2A and 2B, each include wing and body portions, and an iliac crest of is formed on the wings of each of the iliums. The iliac crests, as depicted in FIGS. 2A and 2B, extend from posteriorly from an anterior superior iliac spine to an posterior superior iliac spine of each of the wings of the iliums. The wings of the iliums on the left and the right coxal bones on the posterior sides thereof each include posterior gluteal surfaces (FIG. 2A) to which gluteus maximus muscles, gluteus medius muscles, and gluteus minimus muscles are attached. The gluteus maximus and the gluteus minimus muscles are attached to the posterior gluteal surfaces at and adjacent the iliac crests of each of the wings of the iliums. Bone anchors (with or without threads) used to stabilize the sacroiliac joints using conventional surgical and conventional stabilization techniques have been inserted through portions of the iliac crests and/or portions of the posterior gluteal surfaces adjacent the iliac crests and into the sacrum. Additionally, the wings of the iliums on the left and right coxal bones on the anterior sides thereof each include an iliac fossa surface (FIG. 2B), and the left and right coxal bones on the medial sides thereof each include an iliac tuberosity (FIGS. 2B, 4A, and 4B) adjacent the corresponding posterior superior iliac spine. The auricular surfaces of the left and right coxal bones are formed between the corresponding iliac fossa surfaces and the iliac tuberosities.

Figure 3A:
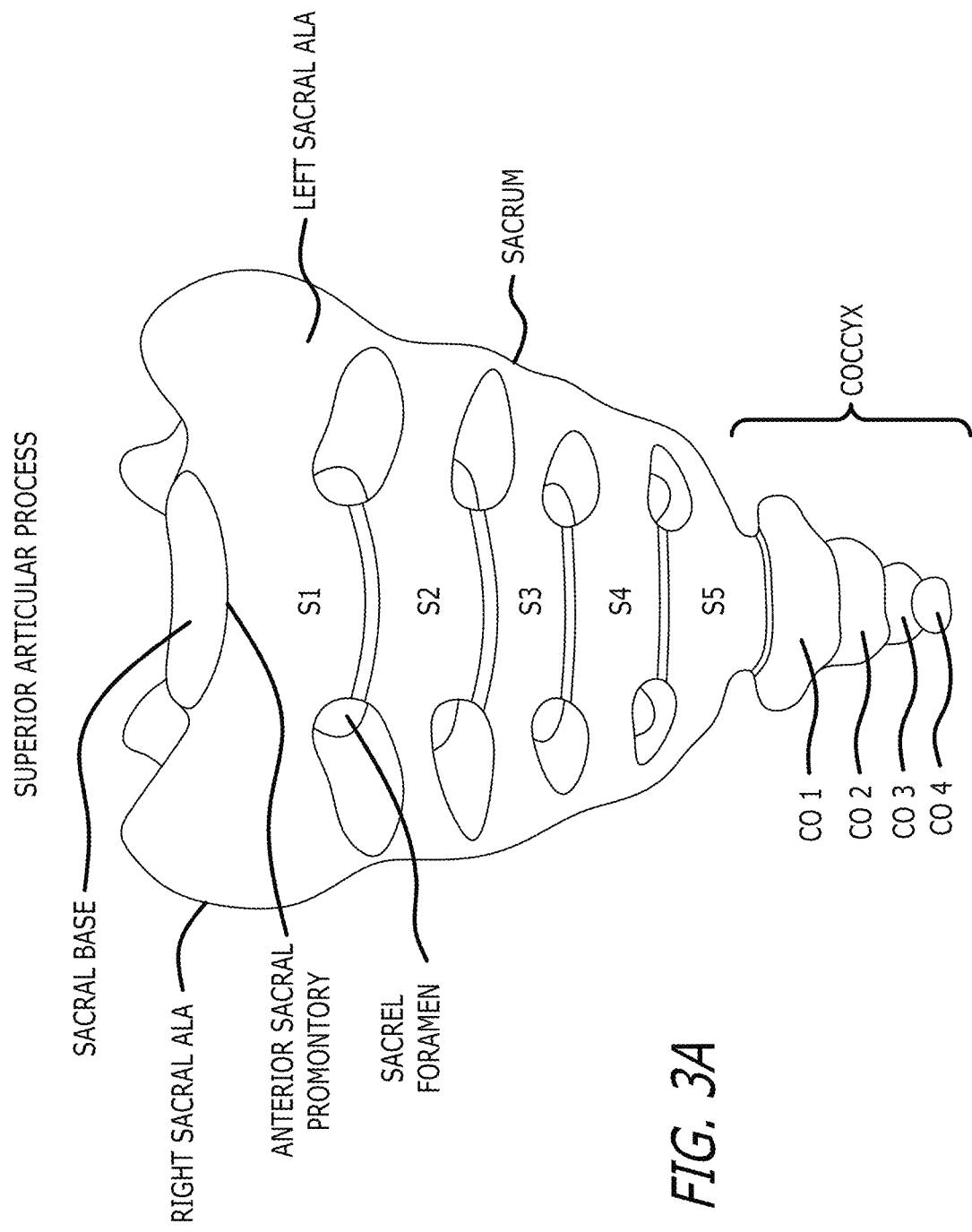
FIG. 3A is an anterior representative view illustrating the sacrum of the pelvis.
Figure 3B:
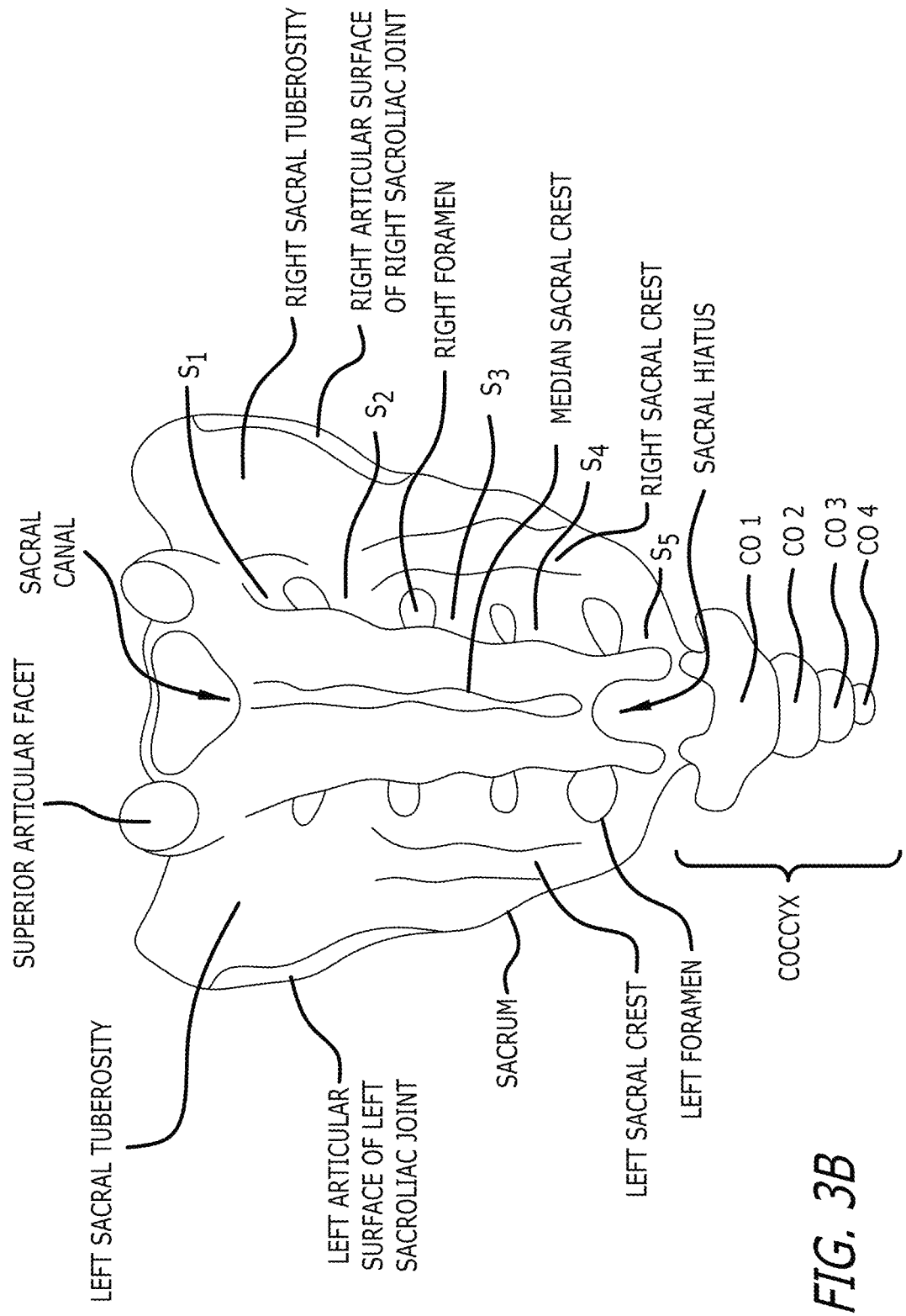
FIG. 3B is a posterior representative view illustrating the sacrum of the pelvis.
Figure 4B:
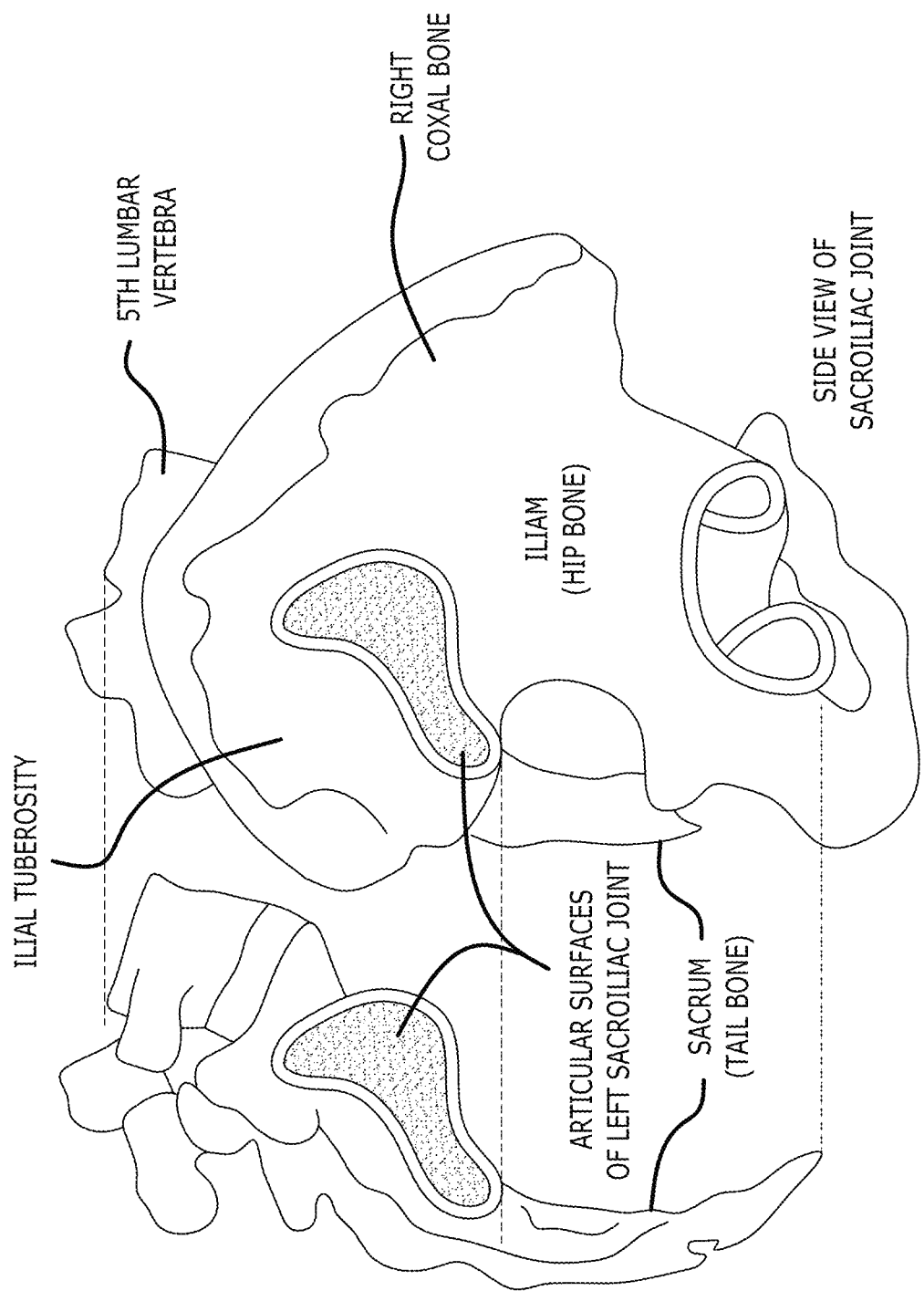
FIG. 4B is a right-side exploded (partially phantom) representative view of a right coxal bone and the sacrum that form the right sacroiliac joint.

The sacrum, as depicted in FIG. 3A, on the anterior side thereof includes a base, an anterior sacral promontory, S1, S2, S3, S4, and S5, left and right anterior sacral foramen on either sides of S1, S2, S3, S4, and S5, and left and right sacral ala on either sides of the anterior sacral promontory and S1. The sacrum on the posterior side thereof, as depicted in FIG. 3B, includes a median sacral crest, left and right lateral crests on either side of the median sacral crest, left and right posterior sacral foramen between the median sacral crest and a corresponding one of the left and the right lateral crests, and left and right sacral tuberosities adjacent a corresponding one of the left and the right lateral crests. The left and the right auricular surfaces of the sacrum are formed between the left tuberosity and the left sacral ala and between the right tuberosity and the right sacral ala, respectively.

The left and the right sacroiliac joints are the largest axial joints in the human body, and can be a significant source of lower back pain. As depicted in FIGS. 1, 2A, and 2B, the left and the right sacroiliac joints join the left and the right coxal bones to the sacrum on the left side and the right side thereof, respectively. The left and the right sacroiliac joints serve in transferring loads between a lumber spine and lower extremities of the human body by transferring such loads between the sacrum and the left coxal bone and the right coxal bone. The sacroiliac joints have limited ranges of movement with around 1.5° of axial rotation and an average of <2 mm of translation. Sacroiliitis is joint pain and inflammation resulting caused by dysfunction of the sacroiliac joints.

As part of the left and the right sacroiliac joints, the left and the right auricular surfaces of the sacrum interface with the left and the right auricular surfaces, respectively, of the left and the right coxal bones across the sacroiliac joints.

Each of the sacroiliac joints are synovial diarthrosis-amphiarthrosis joints surrounded by a fibrous joint capsule, and include two types of cartilage that affords articulation of the above-discussed auricular surfaces of sacroiliac joints relative to one another. Hyaline cartilage is provided on the sacral sides and fibrocartilage is provided on the iliac crest sides of the sacroiliac joints. The cartilage at the sacral sides and the iliac crest sides form articular surfaces via contact therebetween. Various ligaments are associated with the sacroiliac joints. These ligaments surround the joint capsules and serve to stabilize the sacroiliac joints. Each of the sacroiliac joints include main ligaments in the form of an interosseous sacroiliac ligament, an anterior sacroiliac ligament, and a posterior sacroiliac ligament. Additionally, the sacroiliac joints are surrounded by a multitude of muscles used to stabilize the joint. Damage to nerves located adjacent the sacroiliac joint, and damage to the joint capsules, the cartilage, the ligaments, and/or the muscles associated with the sacroiliac joints can cause sacroiliitis. Articulation of the sacroiliac joints can exacerbate such joint pain and inflammation.

Stabilization of the sacroiliac joints of a patient has been used to treat the pain by constraining movement of the sacroiliac joints. The conventional surgical and the conventional stabilization techniques typically use a "bond-nailing effect" with a multitude of bone anchors or fasteners (with or without threads) generally laterally or posterolaterally inserted and implanted in a substantially parallel fashion to one another through portions of the iliac crests and/or portions of the posterior gluteal surfaces adjacent the iliac crests, through the corresponding sacroiliac joints, and into the sacrum to hold the left and the right iliums (of the left or the right coxal bones), and the sacrum in position relative to one another and constrain movement therebetween. Ultimately, when using the typical conventional surgical and stabilization techniques including exemplary use of three (3) bone screws 100, they are positioned side-by-side, adjacent to one another in substantially parallel arrangement to one another through portions of the pelvis. A clinical example of using the conventional surgical and the conventional stabilization techniques using the substantially parallel arrangement of the three (3) bone screws 100 to stabilize a right sacroiliac joint of a pelvis is depicted in the radiographic images of FIGS. 6A and 6B, and portions of FIGS. 18-21. To illustrate, FIGS. 6A, 6B, and 18-21 depict the three (3) bone screws 100 implanted substantially parallelly to one another through portions of an iliac crest and/or portions of posterior gluteal surfaces adjacent the iliac crest of an ilium of a right coxal bone, across at least portions of the right sacroiliac joint, and into a right side of a sacrum.

After conventional implantation thereof, the three (3) bone screws have mid-longitudinal axes 102 that are aligned substantially parallel to one another at similar angles. In particular, the longitudinal axes 102 of the three (3) bone screws 100, as depicted in FIGS. 18-21, are each angled at approximately 65 degrees+/−10 degrees relative to an anterior side of a coronal plane extending through the center of the pelvis, angled at approximately 20 degrees+/−5 degrees relative to a cephalad side of an axial plane extending through the center of the pelvis, and angled at approximately 30 degrees+/−5 degrees relative to a right side of a sagittal plane extending through the center of the pelvis.

It is noted, however, that the mechanical strength of the connection using the parallel alignment of the three (3) bone screws of the conventional surgical and the conventional stabilization techniques is not ideal. The parallel alignment of the three (3) bone screws, and the potentially poor strength of the sacral bone compared to the bone of the left and the right iliums and the corresponding modest sacral fixation struggle to resist movement of a sacroiliac joint under the loads applied thereto. While the parallel alignment of the three (3) bone screws and the modest sacral fixation can be capable of resisting movement of the sacroiliac joint in some directions, the parallel alignment of the three (3) bone screws and the modest sacral fixation can be limited in its resistance of movement in other directions. Methods according to the present disclosure for facilitating stabilization of a sacroiliac joint includes surgical and stabilization techniques are provided to overcome the limitations of the conventional surgical and the conventional fusion techniques.

The surgical and the stabilization techniques according to the present disclosure afford implantation of a multitude of bone anchors or fasteners (with or without threads) at different angles and placements in a pelvis of the patient to facilitate stabilization of one or both of the sacroiliac joints. The stabilization of the sacroiliac joints can facilitate fusion thereacross between left and right sides of a sacrum and corresponding left and right coxal bones of the pelvis. And although fusion of one or both of the sacroiliac joints can be a preferred outcome of the surgical and stabilization techniques of the present disclosure, mechanically securing and stabilizing one or both of the sacroiliac joints without fusion can be advantageous for certain patients. Additionally, although bone screws 10 are discussed below, other bone anchors or fasteners, for example, such as pins and posts with ratchets and/or teeth can be inserted and implanted in similar fashion as the bone screws 10. The bone anchors or fasteners can have different cross-sectional shapes (such as, for example, hexagonal or octagonal shapes), and can include cannulations and/or fenestrations therealong to facilitate extrusion of flowable materials such as bone cement, bone graft, biodegradable polymers, or other bone-growth-promoting substances, etc., which can interdigitate and/or integrate with adjacent bone structure via perfusion methods.

As discussed below, the different angles and the placements of the multitude of the bone screws 10 increase the mechanical strength of the connection formed thereby in comparison to the conventional surgical and the conventional stabilization techniques described above. As depicted in FIGS. 6A, 6B, and 18-22, three (3) of the bone screws 10 (a first bone screw 10A, a second bone screw 10B, and a third bone screw 10C) are inserted and implanted in an arrangement in an area across and/or adjacent the left sacroiliac joint of the pelvis generally indicated by reference 12A. As discussed below, the first bone screw 10A, the second bone screw 10B, and the third bone screw 10C are inserted and implanted at different angles and placements relative to one another into portions of the area 12A. Furthermore, the right sacroiliac joint, as depicted in FIGS. 8-17, can also be fused using three (3) bone screws 10 (the first bone screw 10A, the second bone screw 10B, and the third bone screw 10C) inserted and implanted in a mirrored arrangement in an area across and/or adjacent the right sacroiliac joint generally indicated by the reference 12B. As discussed below and in similar fashion, the first bone screw 10A, the second bone screw 10B, and the third bone screw 10C are inserted and implanted at different angles and placements relative to one another into portions of the area 12B. Although at least three (3) of bone screws 10 are utilized, additional bone screws 10 can be used, and these additional bone screws 10 can also be inserted and implanted at different additional angles and placements relative to one another and each of the first bone screw 10A, the second bone screw 10B, and the third bone screw 10C in the areas 12A and 12B.

Figure 5:
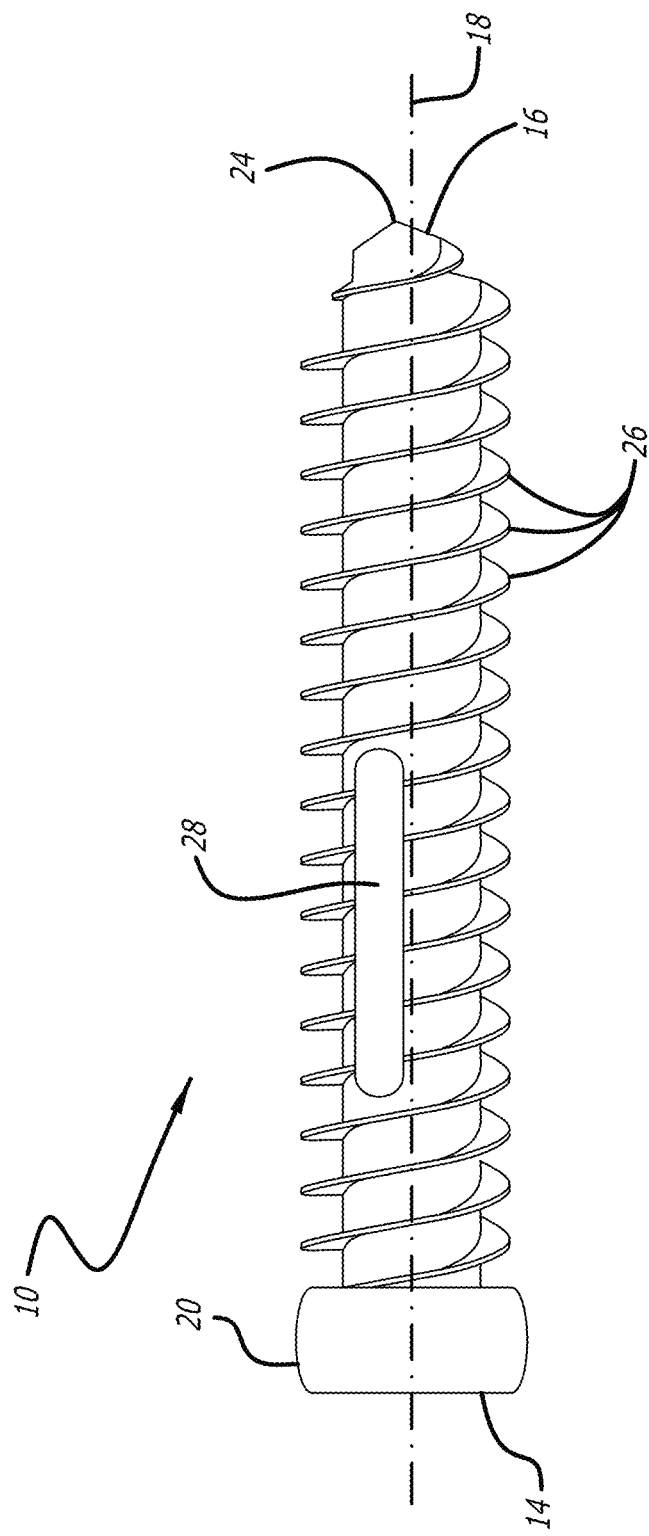
FIG. 5 is a side, elevational view of an exemplary bone screw that can be used with surgical and stabilization techniques according to the present disclosure.
Figure 6A:
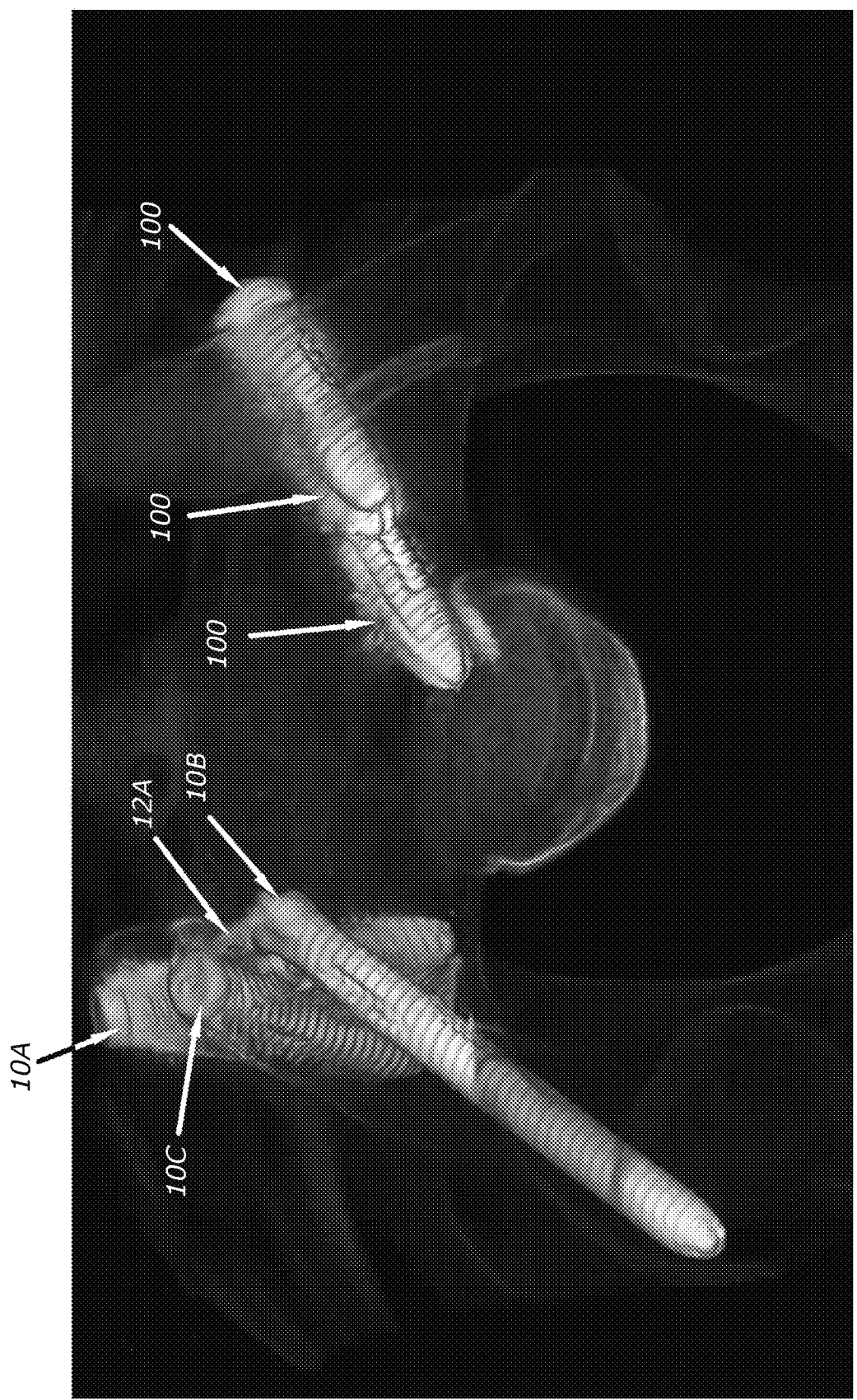
FIG. 6A is a radiographic axial cross-sectional view in a cephalad direction of a portion of a pelvis with three bone screws positioned on a right-side of the pelvis resulting from use of conventional surgical and conventional stabilization techniques used to facilitate stabilization of the right sacroiliac joint, and with three bone screws positioned on a left-side of the pelvis resulting from use of the surgical and the stabilization techniques according to the present disclosure used to facilitate stabilization of the left sacroiliac joint.
Figure 6B:
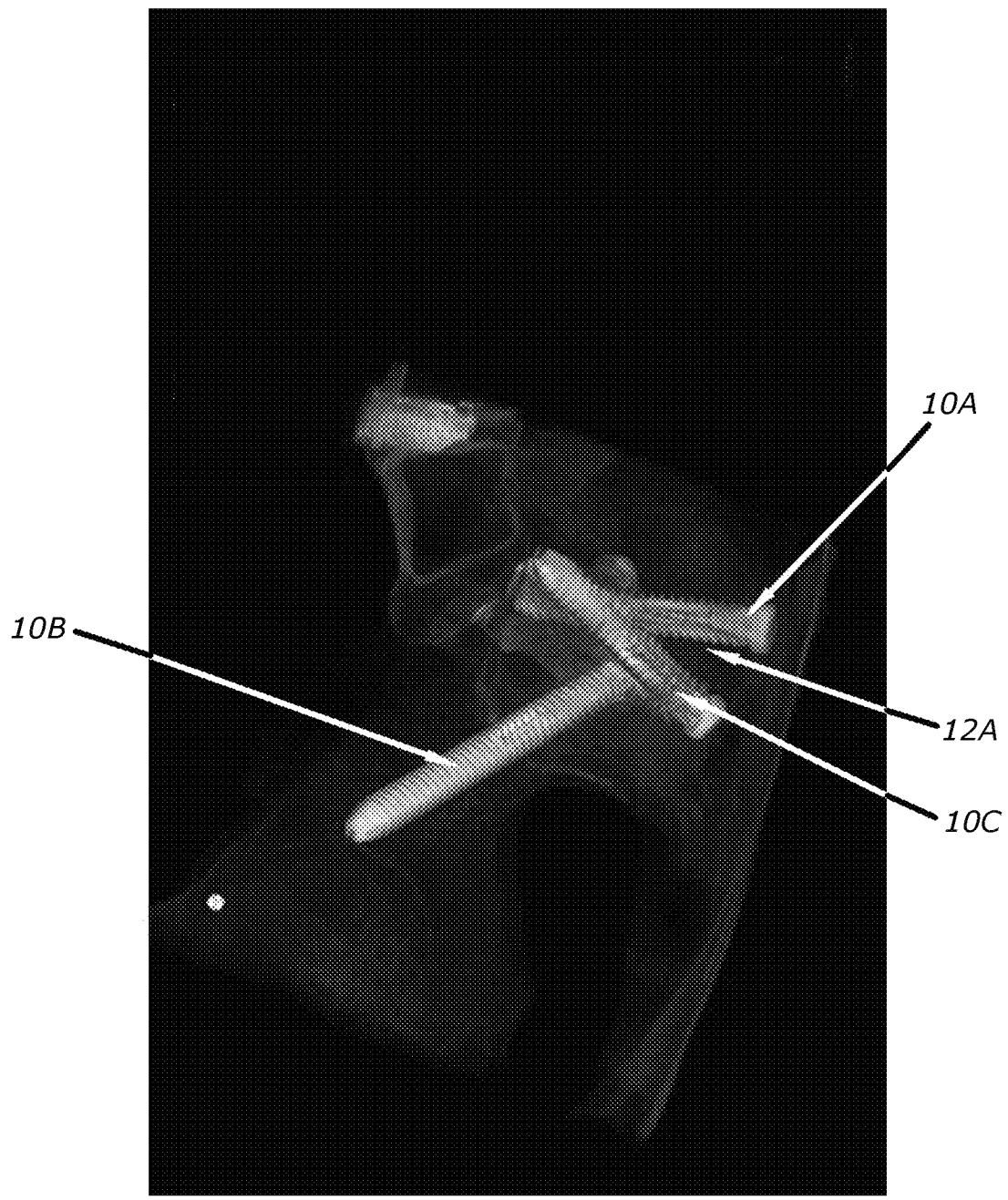
FIG. 6B is a radiographic sagittal cross-sectional view from a left lateral direction of a portion of the pelvis of FIG. 6A with the bone screws positioned on the left-side of the pelvis resulting from the surgical and the stabilization techniques according to present disclosure.
Figure 7:
FIG. 7 is a radiographic axial cross-sectional view in a caudal direction of a portion of a pelvis before placement of bone screws using the surgical and the stabilization techniques according to the present disclosure.

Each of the bone screws 10 can be non-hollow, partially hollow, or hollow, can have similar or different diameters, and/or can have similar or different lengths. Exemplary bone screws are disclosed in U.S. Pat. No. 11,813,001, which is hereby incorporated by reference herein. As depicted in FIG. 5, each of the bone screws 10 (including the first bone screw 10A, the second bone screw 10B, and the third bone screw 10C) can include a proximal end 14, an opposite distal end 16, and a mid-longitudinal axis 18 extending through the proximal end 14 and the distal end 16. Furthermore, as depicted in FIGS. 8, 11, 14, 17, and 18-22, the first bone screw 10A can have a mid-longitudinal axis 18A, the second bone screw 10B can have a mid-longitudinal axis 18B, and the third bone screw 18C can have a mid-longitudinal axis 18C extending through the respective proximal ends 14 and the respective distal ends 16. Additionally, as depicted in FIG. 5, each of the bone screws 10 can include a head portion 20 provided at and adjacent the proximal end 14, a shank portion 22 extending from the head portion 20 toward the distal end 16, a tip portion 24 at the distal end 16, and threads 26 provided along all or portions of the shank portion 22 and the tip portion 24. Each of the bone screws 10 can be partially hollow with various holes 28 extending through the shank portions 22 transversely across the respective mid-longitudinal axes 18A, 18B, and 18C. The various holes 28 can be packed with, for example, bone cement, bone graft, biodegradable polymers, or other bone-growth-promoting substances, etc. prior to or after insertion and implantation of the bone screws 10 into the pelvic areas 12A and 12B to facilitate bone ingrowth and fusion of bone in the areas 12A and 12B across and/or adjacent the left and the right sacroiliac joints, respectively.

Figure 15:
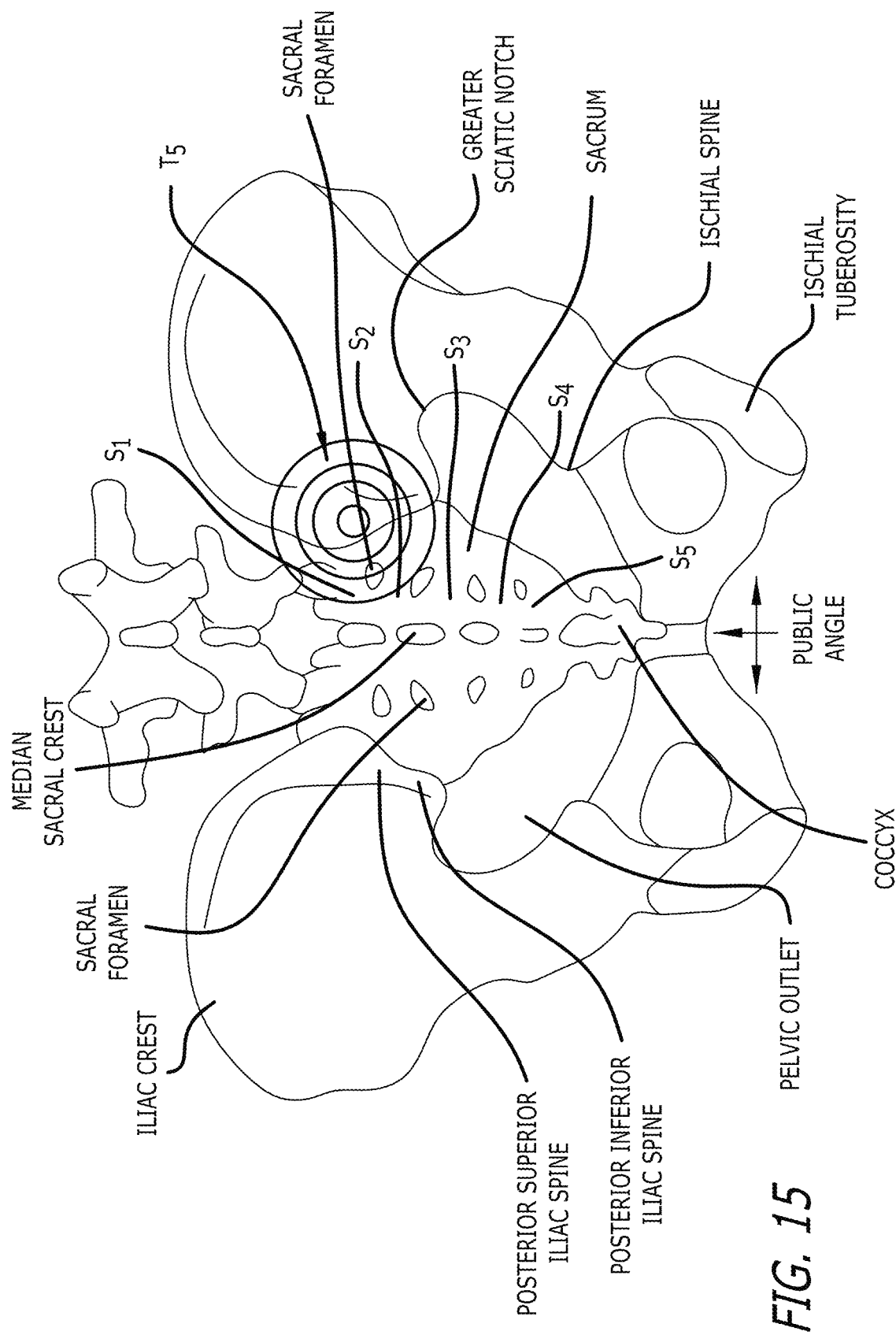
FIG. 15 is a posterior representative view similar to FIG. 2A illustrating the pelvis, and depicting a starting point for placement of the third bone screw of FIG. 14 to facilitate stabilization of the right sacroiliac joint.
Figure 16:
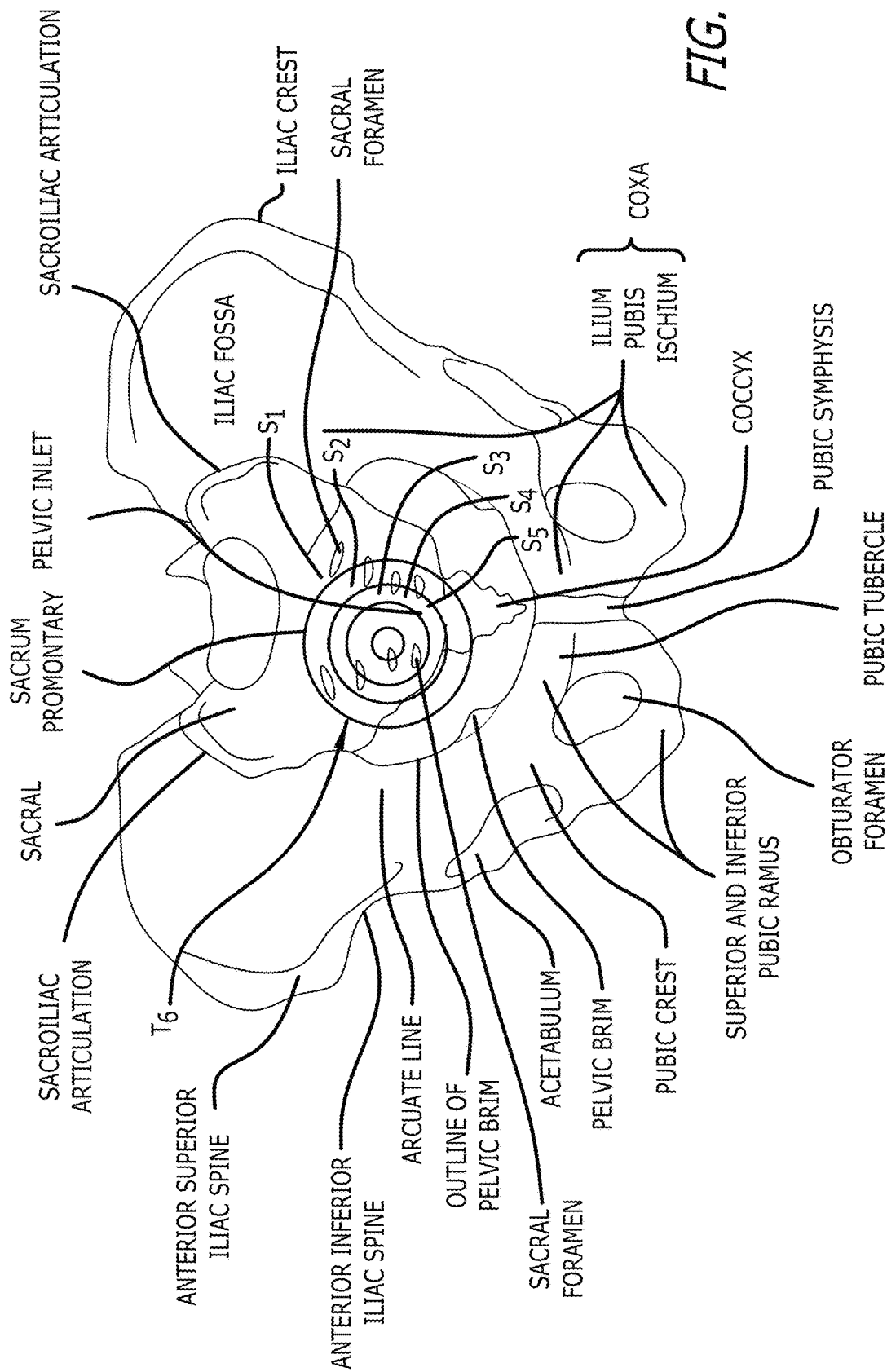
FIG. 16 is an anterior representative view similar to FIG. 2B illustrating the pelvis, and depicting a finishing point for placement of the third bone screw of FIG. 14 to facilitate stabilization of the right sacroiliac joint.
Figure 17:
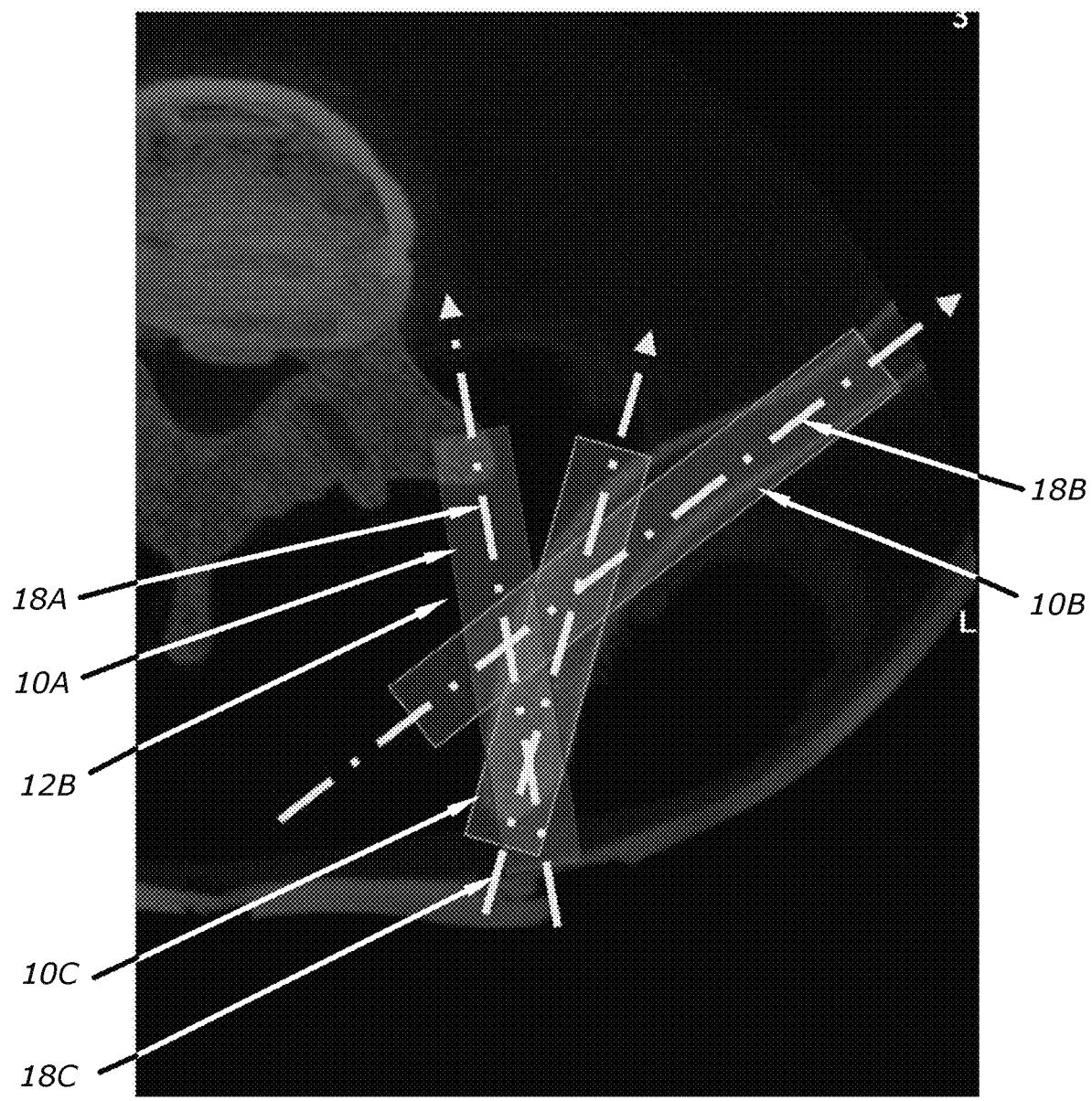
FIG. 17 is a radiographic axial cross-sectional view in a caudal direction of a portion of the pelvis of FIG. 7 showing placement of the first bone screw, the second bone screw, and the third bone screw of the surgical and the stabilization techniques according to the present disclosure to facilitate stabilization of the right sacroiliac joint.
Figure 18:
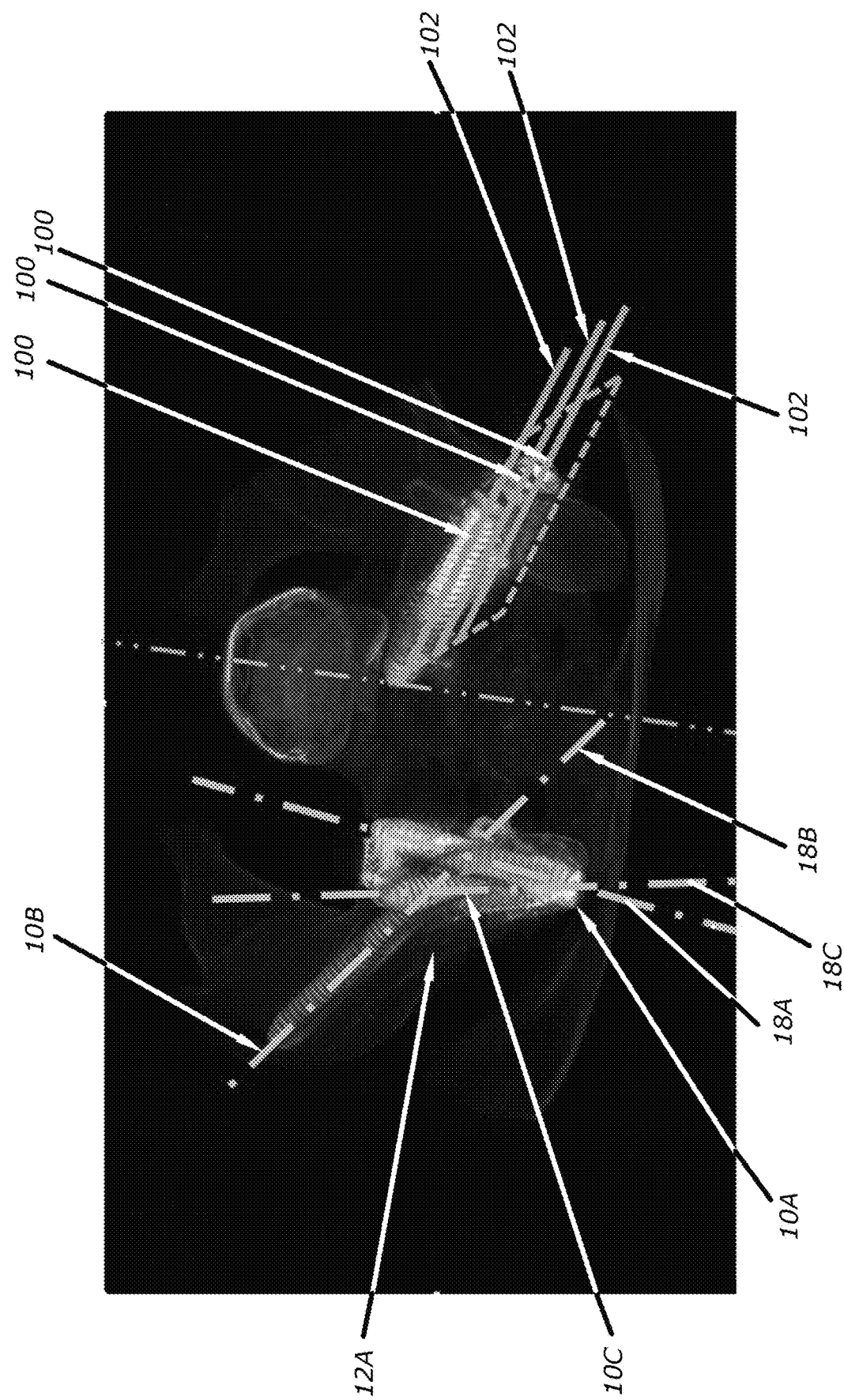
FIG. 18 is a radiographic axial cross-sectional view in a caudal direction at a first axial level of a portion of a pelvis showing axes of the three bone screws used in the conventional surgical and the conventional stabilization techniques positioned on the right side of the pelvis, and axes of the first bone screw, the second bone screw, and the third bone screw used in the surgical and the stabilization techniques according to the present disclosure positioned on the left side of the pelvis.
Figure 19:
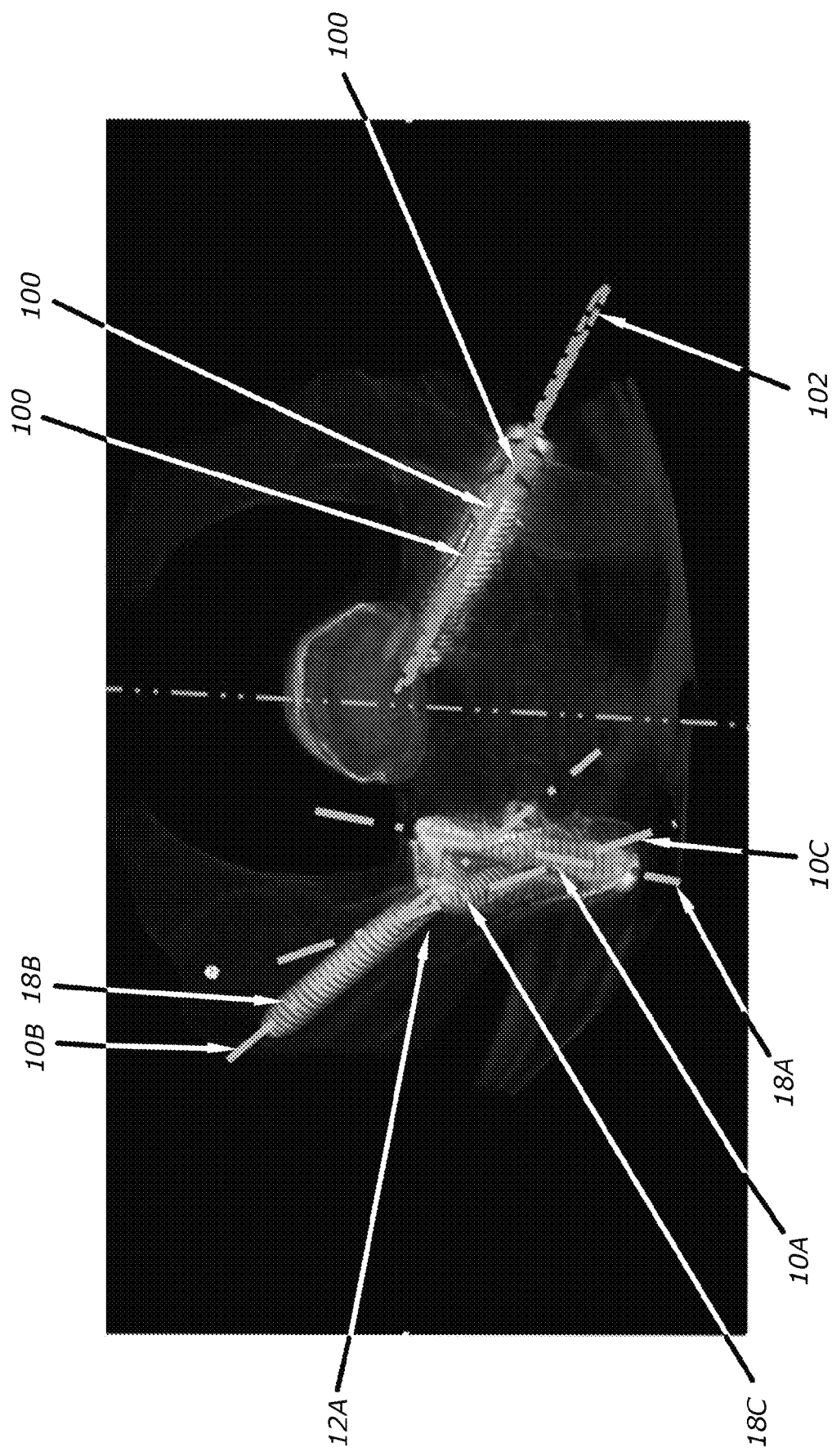
FIG. 19 is a radiographic axial cross-sectional view in a caudal direction at a second axial level of a portion of the pelvis of FIG. 18 showing the axes of the three bone screws used in the conventional surgical and the conventional stabilization techniques positioned on the right side of the pelvis, and the axes of the first bone screw, the second bone screw, and the third bone screw used in the surgical and the stabilization techniques according to the present disclosure positioned on the left side of the pelvis.
Figure 20:
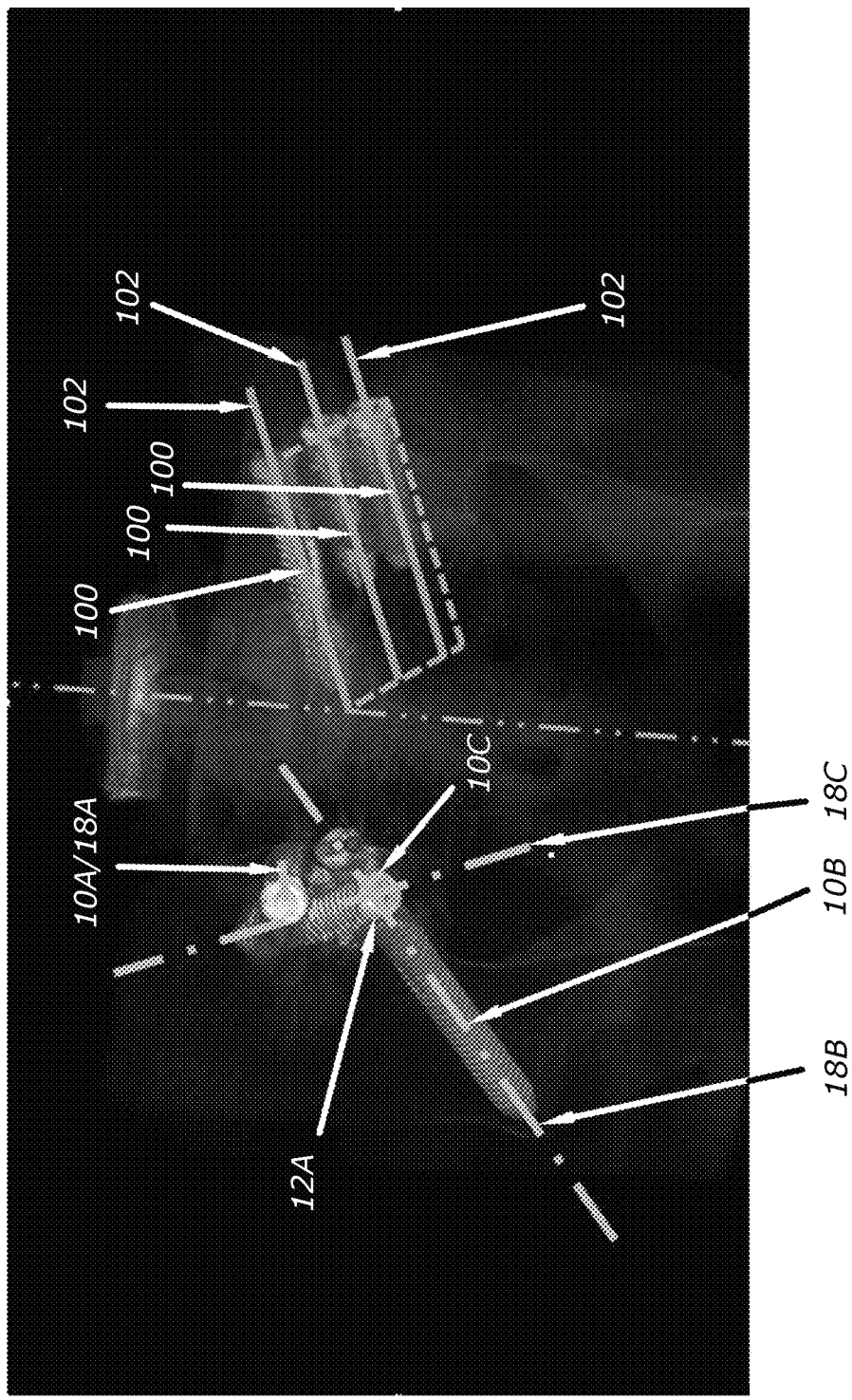
FIG. 20 is a radiographic coronal cross-sectional view from a posterior direction of a portion of the pelvis of FIG. 18 showing the axes of the three bone screws used in the conventional surgical and the conventional stabilization techniques position on the right side of the pelvis, and the axes of the first bone screw, the second bone screw, and the third bone screw used in the surgical and the stabilization techniques according to the present disclosure positioned on the left side of the pelvis.
Figure 21:
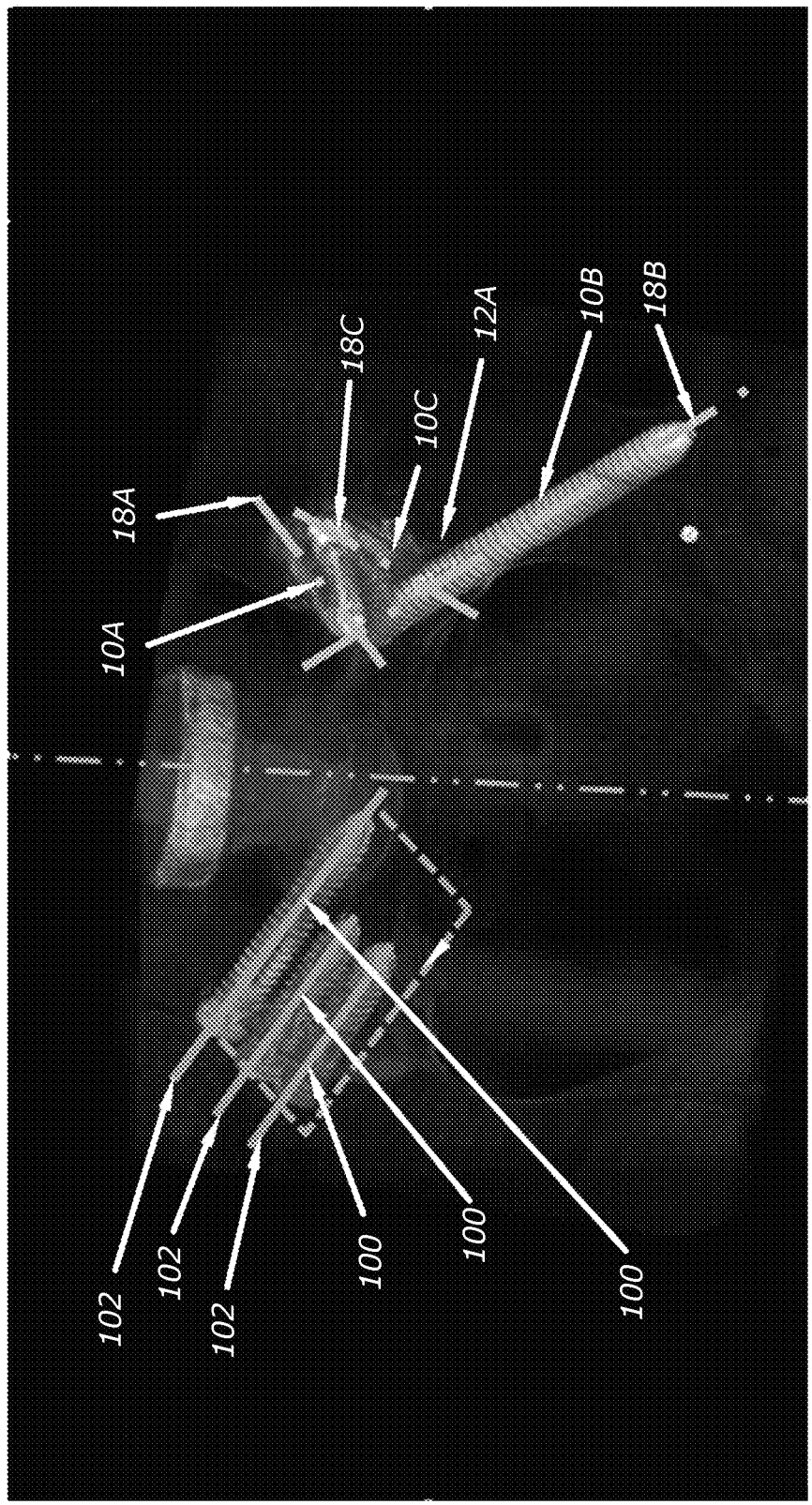
FIG. 21 is a radiographic coronal cross-sectional view from an anterior direction of a portion of the pelvis of FIG. 18 showing the axes of the three bone screws used in the conventional surgical and the conventional stabilization techniques position on the right side of the pelvis, and the axes of the first bone screw, the second bone screw, and the third bone screw used in the surgical and the stabilization techniques according to the present disclosure positioned on the left side of the pelvis.
Figure 22:
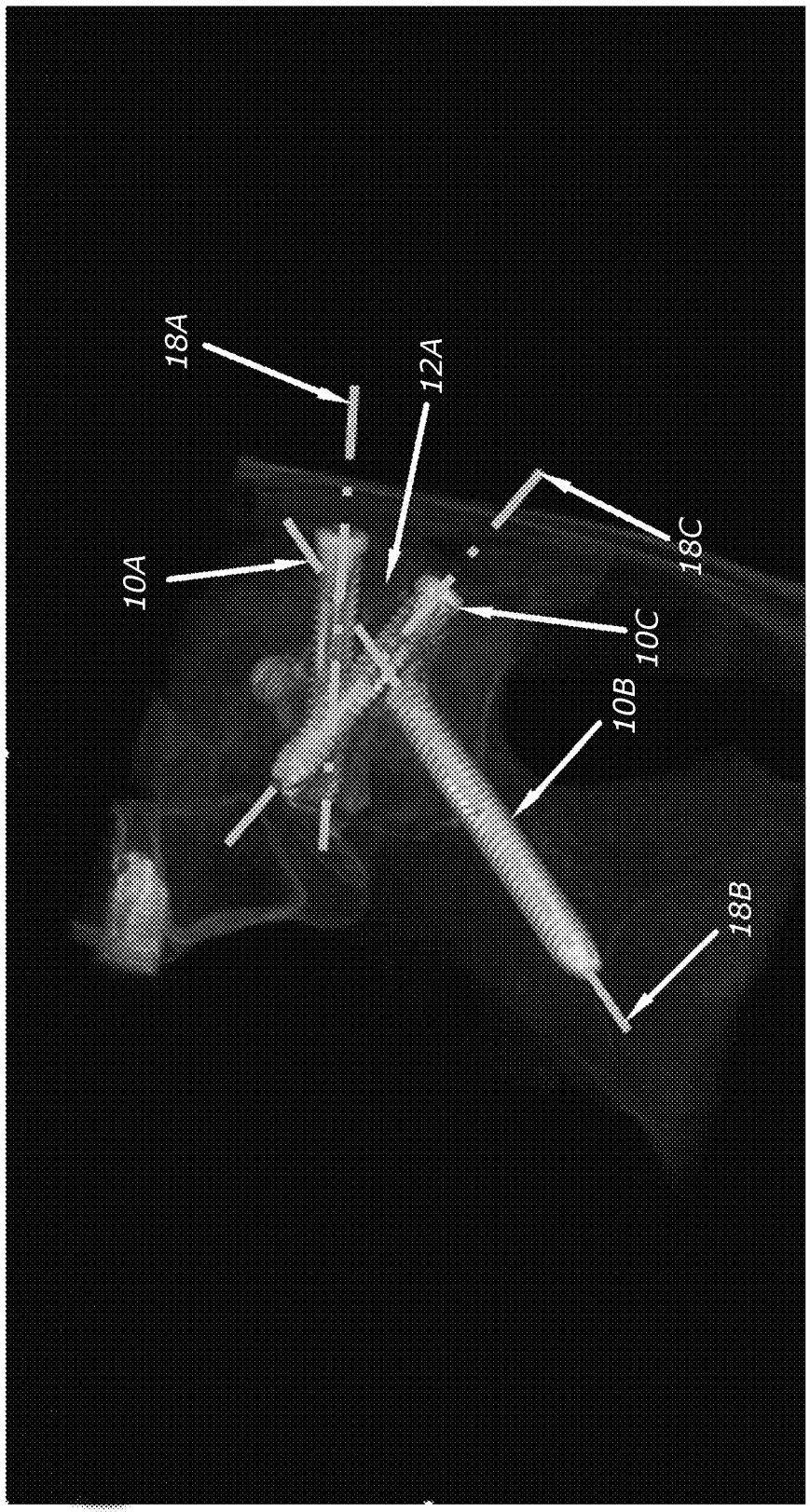
FIG. 22 is a radiographic sagittal cross-sectional view from a left lateral direction of a portion of the pelvis of FIG. 18 showing the axes of the first bone screw, the second bone screw, and the third bone screw used in the surgical and the stabilization techniques according to the present disclosure positioned on the left side of the pelvis.

Using the surgical and the stabilization techniques according the present disclosure, as depicted in FIGS. 8-16, the first bone screw 10A (FIGS. 8-10), the second bone screw 10B (FIGS. 11-13), and the third bone screw 10C (FIGS. 14-16) can be inserted and implanted sequentially at different angles and placements into portions of the area 12B across and/or adjacent the right sacroiliac joint of the pelvis of the patient that results in the arrangement of FIG. 17. Although the stabilization of the right sacroiliac joint is illustrated in FIGS. 8-17, the left sacroiliac joint can be stabilized in a similar manner. And, while FIGS. 9-16 describe potential insertion sequence of bone anchors or fasteners, where the first bone screw 10A is inserted first, the second bone screw 10B is inserted second, and the third bone screw 10C is inserted third, the order can be rearranged as desired. Each of the bone anchors or fasteners (e.g., the first bone screw 10A, the second bone screw 10B, and the third bone screw 10C) are inserted generally laterally through one or more incisions in a posterior sacroiliac area commonly referred to as a lower back region or a buttocks region that is adjacent the lower back region of a patient. Various targets in FIGS. 9 and 10 (first and second targets $T_1$ and $T_2$), in FIGS. 12 and 13 (third and fourth targets $T_3$ and $T_4$, and in FIGS. 15 and 16 (fifth and sixth targets $T_5$ and $T_5$) are provided to illustrate insertion and implantation trajectories (and corresponding angles and placements) of the bone anchors or fasteners (e.g., the first bone screw 10A, the second bone screw 10B, and the third bone screw 10C). To illustrate, the targets $T_1$, $T_3$, and $T_5$ depict approximate entry areas into bone for the first bone screw 10A, the second bone screw 10B, and the third bone screw 10C, respectively. And, targets $T_2$, $T_4$, and $T_6$ depict approximate exit areas for corresponding axes of the first bone screw 10A, the second bone screw 10B, and the third bone screw 10C, respectively.

In a preferred embodiment, the entry areas defined by the targets $T_1$, $T_3$, and $T_5$ are potential locations for entry points of the first bone screw 10A, the second bone screw 10B, and the third bone screw 10C, respectively and the precise location of the entry points therefor can depend on, for example, anatomical structures of each patient. As an example, it is desirable to maximize contact of the bone anchors or fasteners with cortical bone, and thus, the insertion and implantation trajectories defined by the entry points in the targets $T_1$, $T_3$, and $T_5$, and exit points of the corresponding axes of the first bone screw 10A, the second bone screw 10B, and the third bone screw 10C in the targets $T_2$, $T_4$, and $T_6$ can be selected to maximize such contact to increase structural rigidity of connections formed thereby. The selected insertion and implantation trajectories between the targets $T_1$ and $T_2$, between the targets $T_3$ and $T_4$, and between the targets $T_5$ and $T_5$ determine angles and placements of the first bone screw 10A, the second bone screw 10B, and the third bone screw 10C, respectively. Additionally, in a preferred embodiment, the first bone screw 10A and the third bone screw 10C have similar lengths, and the second bone screw 10B is longer than the first bone screw 10A and the third bone screw 10C. The lengths of the first bone screw 10A, the second bone screw 10B, and the third bone screw 10C can be determined by the insertion and implantation trajectories thereof, and the depth of bone available for the corresponding insertion and implantation trajectories. The larger the depth of the bone available for insertion and implantation, the longer the corresponding length of the bone screw can be, and the smaller the depth of the bone available for insertion and implantation, the shorter the corresponding length of the bone screw can be. Maximizing the lengths of the bone anchors or fasteners can also maximize contact thereof with the cortical bone to increase structural rigidity of the connections formed thereby.

Figure 8:
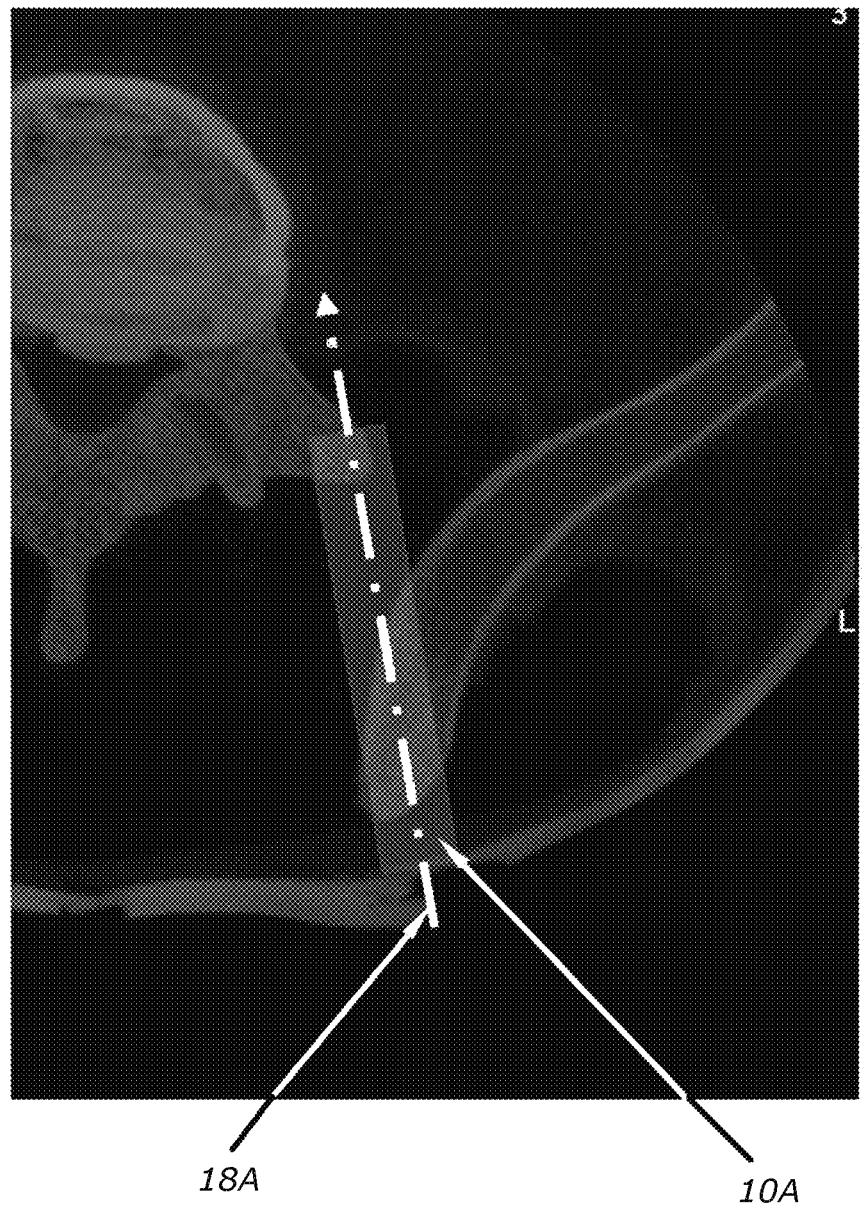
FIG. 8 is a radiographic axial cross-sectional view in a caudal direction of a portion of the pelvis of FIG. 7 showing placement of a first bone screw and an insertion direction therefor used in the surgical and the stabilization techniques according to the present disclosure to facilitate stabilization of a right sacroiliac joint.
Figure 9:
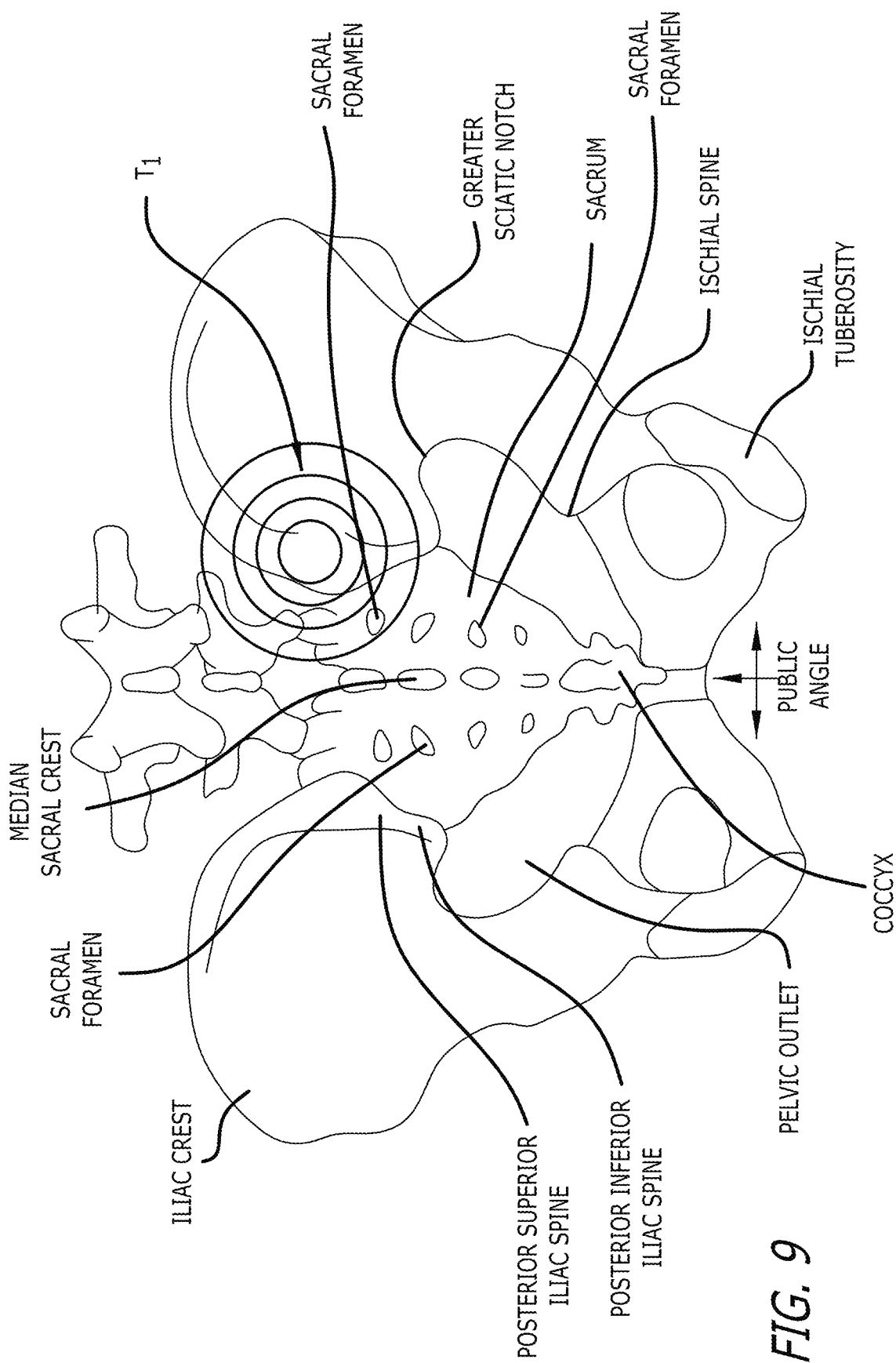
FIG. 9 is a posterior representative view similar to FIG. 2A illustrating the pelvis, and depicting a starting point for placement of the first bone screw of FIG. 8 to facilitate stabilization of the right sacroiliac joint.
Figure 10:
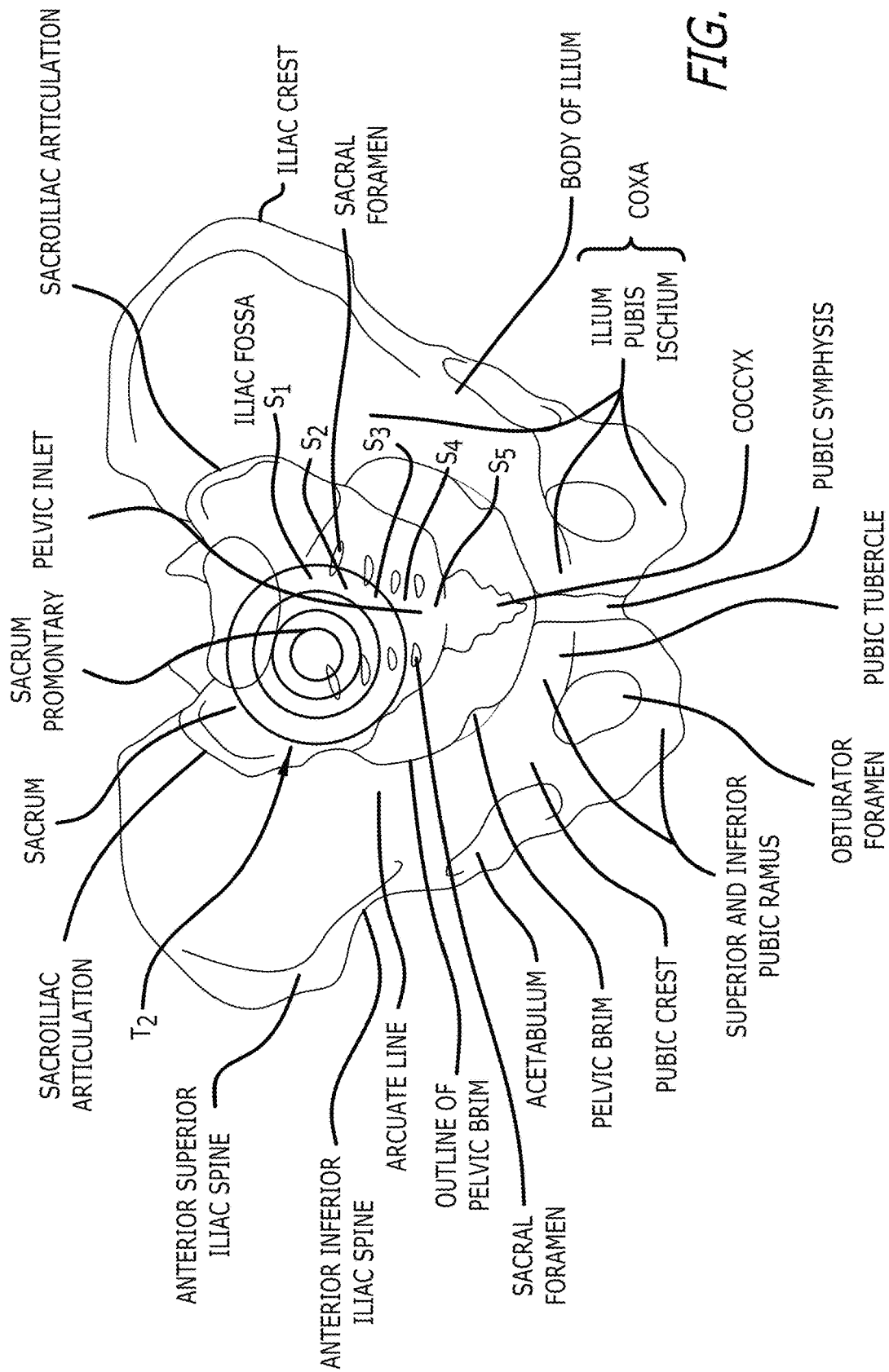
FIG. 10 is an anterior representative view similar to FIG. 2B illustrating the pelvis, and depicting a finishing point for placement of the first bone screw of FIG. 8 to facilitate stabilization of the right sacroiliac joint.

As depicted in FIGS. 8-10, the first bone screw 10A is inserted and implanted on the right side of the patient into a first posterior portion of the posterior superior iliac spine of the iliac crest of the right coxal bone as indicated by a first target $T_1$ in FIG. 9, through the right coxal bone, within, across and/or at least adjacent to a portion of the right sacroiliac joint, and into the sacrum. In a preferred embodiment, the first bone screw 10A (or other bone anchor or fastener) extends through a substantial portion of the sacroiliac joint. To illustrate, the first bone screw 10A can serve as an intra-auricular (or intra-articular) member that runs adjacent and/or between the joint surfaces of the sacrum and the right coxal bone within the right sacroiliac joint to maximize stabilization of the right sacroiliac joint and potential fusion thereof. In doing so, the first bone 10A can run along a substantial length of the right sacroiliac joint. An aperture for receiving the first bone screw 10A can be predrilled at the first target $T_1$ through the right coxal bone (starting at the first posterior portion of the posterior superior iliac spine), the right sacroiliac joint, and the sacrum, or the first bone screw 10A can be self-drilling to form a similar aperture. After implantation, the mid-longitudinal axis 18A of the first bone screw 10A would extend through the first target $T_1$ of FIG. 9 located on the posterior superior iliac spine of the iliac crest of the right coxal bone and through a second target $T_2$ of FIG. 10 located on the right anterior sacral foramen adjacent S1 and S2. Ultimately, the aperture for the first bone screw 10A and the first bone screw 10A itself traverses a 38 mm to 83 mm length portion of the right sacroiliac joint in the area 12B. A distal end of the first bone screw 10A can be approximately 25 mm to 75 mm from the surface of the right anterior sacral foramen adjacent S1 and S2. And, the predrilled aperture and/or the insertion and implantation trajectory of the first bone screw 10A is roughly parallel to a corresponding sacroiliac articular process, and angled at approximately 83 degrees+/−7 degrees relative to an anterior side of a coronal plane extending through the center of the pelvis, angled at approximately 0 degrees+/−3 degrees relative to a cephalad side of an axial plane extending through the center of the pelvis, and angled at approximately 20 degrees+/−8 degrees relative to a right side of a sagittal plane extending through the center of the pelvis. And while the first bone screw 10A (or other bone anchor or fastener) can be utilized as described above, the present disclosure is not so limited. Rather than using the first bone screw 10A (or other bone anchor or fastener), the predrilled aperture, for example, can be filled with bone cement delivered into a biodegradable bag implanted in the predrilled aperture.

Figure 11:
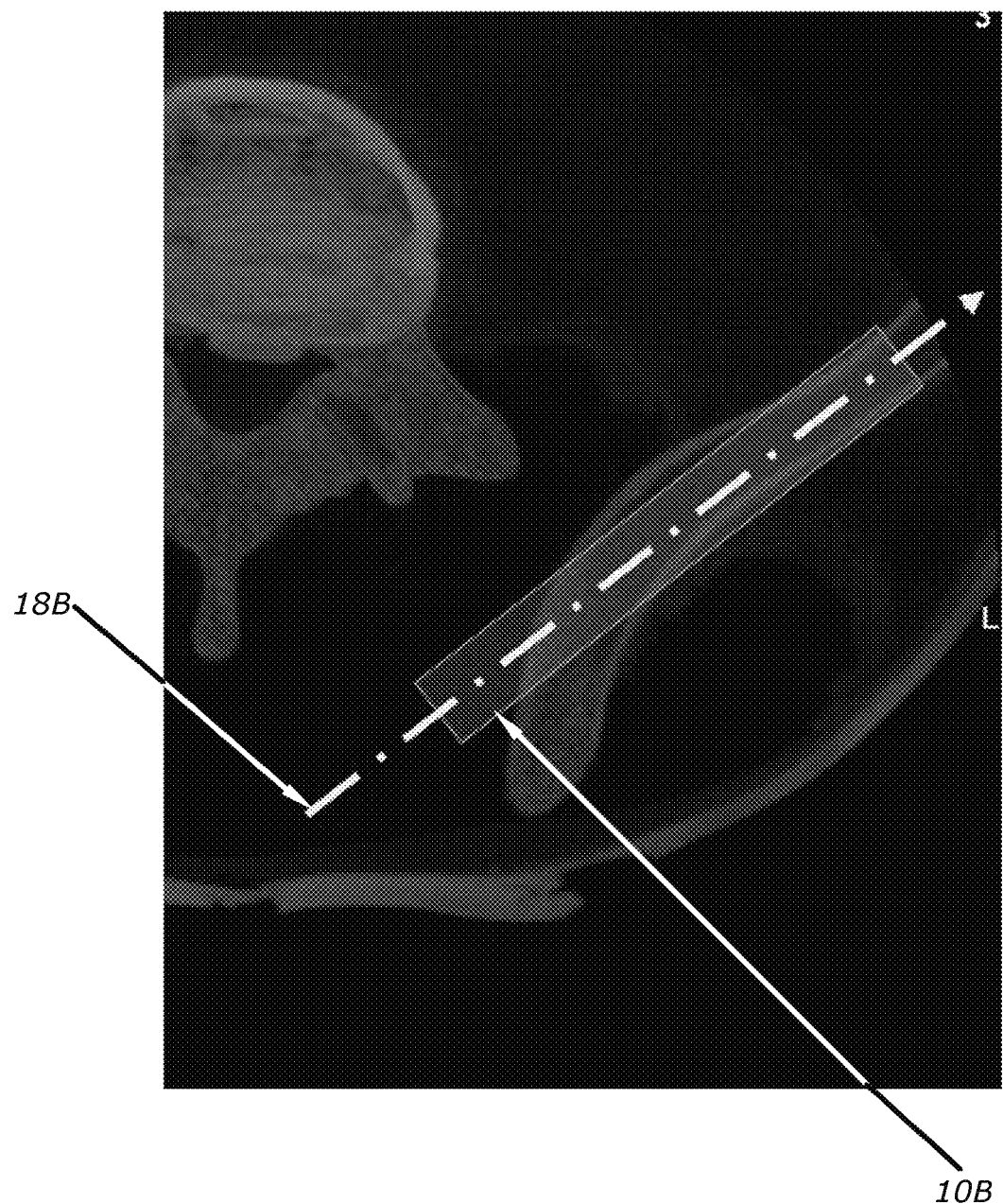
FIG. 11 is a radiographic axial cross-sectional view in a caudal direction of a portion of the pelvis of FIG. 7 showing placement of a second bone screw and an insertion direction therefor used in the surgical and the stabilization techniques according to the present disclosure to facilitate stabilization of the right sacroiliac joint.
Figure 12:
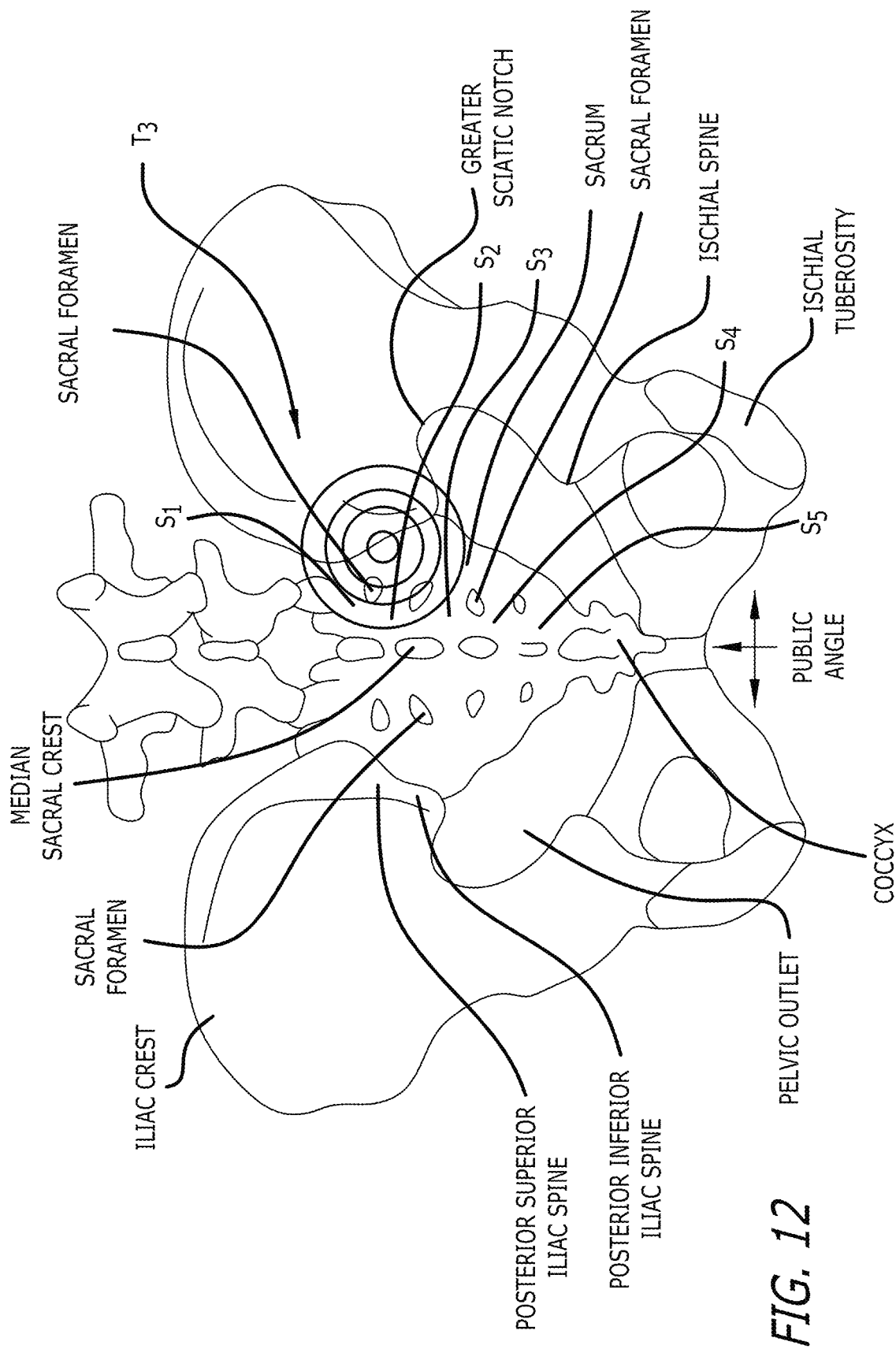
FIG. 12 is a posterior representative view similar to FIG. 2A illustrating the pelvis, and depicting starting point for placement of the second bone screw of FIG. 11 to facilitate stabilization of the right sacroiliac joint.
Figure 13:
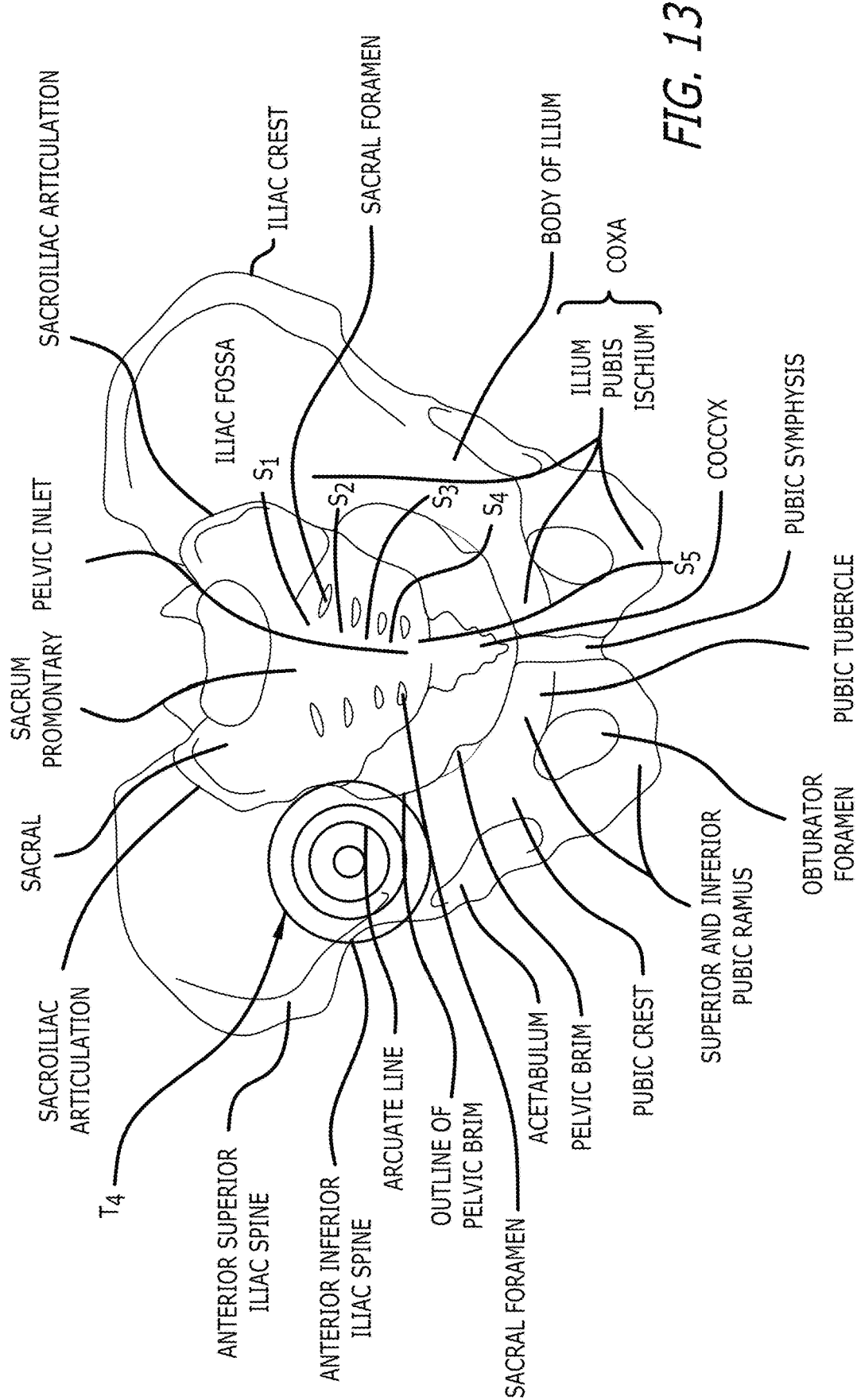
FIG. 13 is an anterior representative view similar to FIG. 2B illustrating the pelvis, and depicting an finishing point for placement of the second bone screw of FIG. 11 to facilitate stabilization of the right sacroiliac joint.

As depicted in FIGS. 11-13, the second bone screw 10B is inserted and implanted on the right side of the patient into a right posterior portion of the sacrum at the right sacral crest or the right sacral tuberosity that potentially can be located behind a first anterior portion of the posterior superior iliac spine of the iliac crest of the right coxal bone as indicated by a third target $T_3$ in FIG. 12, through the sacrum at, for example, the right sacral ala, across a portion of the right sacroiliac joint, and into the right coxal bone. An aperture for receiving the second bone screw 10B can be predrilled at the third target $T_3$ through the right sacral ala (starting at the right posterior portion of the sacrum at the right sacral crest or the right sacral tuberosity), the right sacroiliac joint, and the right coxal bone, or the second bone screw 10B can be self-drilling to form a similar aperture. In a preferred embodiment, the second bone screw 10B can be inserted in a posterior portion of the right sacral wing, S1, or S2, and adjacent the sacral foramen positioned between S1 and S2, and serve as a S1 or S2 alar-iliac screw for fixation of the sacrum and the right coxal bone. The location of the aperture at the third target $T_3$ can be inferior to the location of the aperture at the first target $T_1$. After implantation, the mid-longitudinal axis 18B of the second bone screw 10B would extend through the third target $T_3$ of FIG. 11 located on the right posterior of the sacrum or the first anterior portion of the posterior superior iliac spine of the iliac crest of the right coxal bone located in front of the right posterior portion of the sacrum and through a fourth target $T_4$ of FIG. 13 located on the ilium of the right coxal bone. Ultimately, the aperture for the second bone screw 10B and the second bone screw 10B itself traverses a 34 mm to 150 mm length portion of the right sacroiliac joint in the area 12B. A distal end of the second bone screw 10B can be approximately 20 mm to 130 mm from the surface of the ilium of the right coxal bone, And, the predrilled aperture and/or the insertion and implantation trajectory of the second bone screw 10B is angled at approximately 45 degrees+/−25 degrees relative to an anterior side of a coronal plane extending through the center of the pelvis, angled at approximately 35 degrees+/−25 degrees relative to a cephalad side of an axial plane extending through the center of the pelvis, and angled at approximately 40 degrees+/−30 degrees relative to a right side of a sagittal plane extending through the center of the pelvis.

Figure 23A:
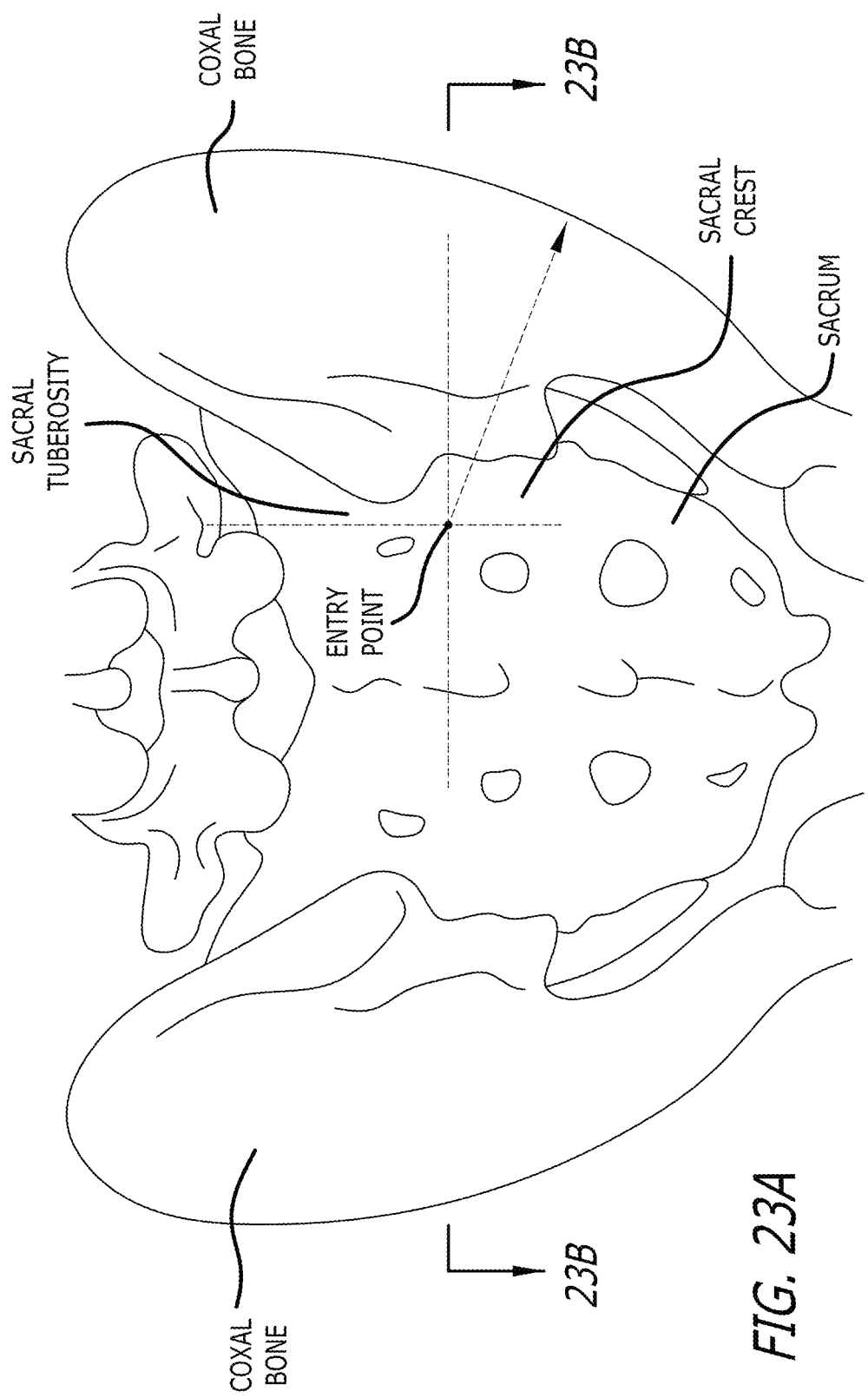
FIG. 23A is a posterior representative view illustrating the pelvis showing an entry point for the second bone screw in the right side of the sacrum to facilitate stabilization of the right sacroiliac joint.
Figure 23B:
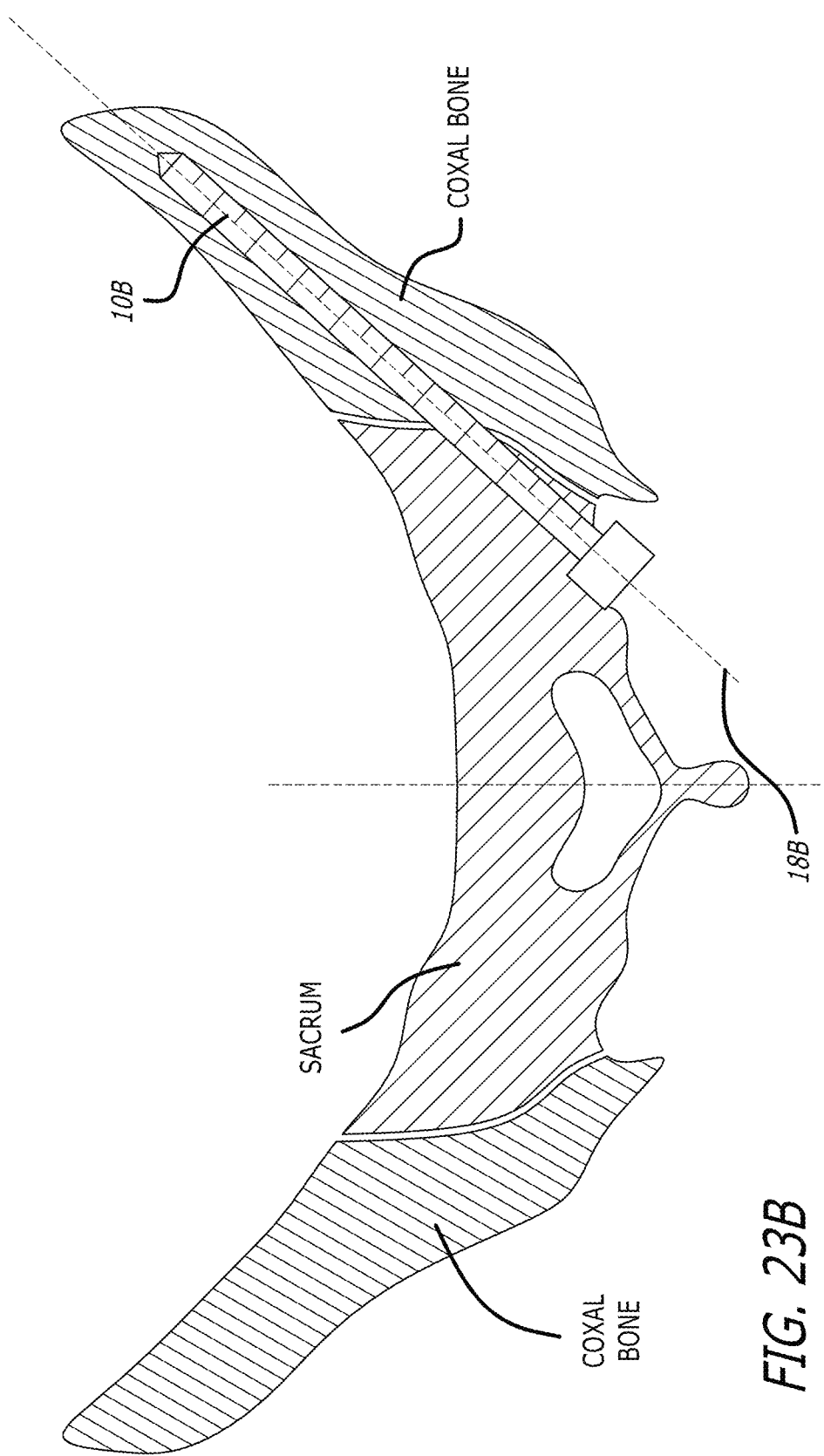
FIG. 23B is a cross-sectional representative view illustrating a cross-section of the pelvis along Line 23B-23B of FIG. 23A showing the second bone screw and the trajectory thereof through the sacrum, the right sacroiliac joint, and the right coxal bone to facilitate stabilization of the right sacroiliac joint.
Figure 23C:
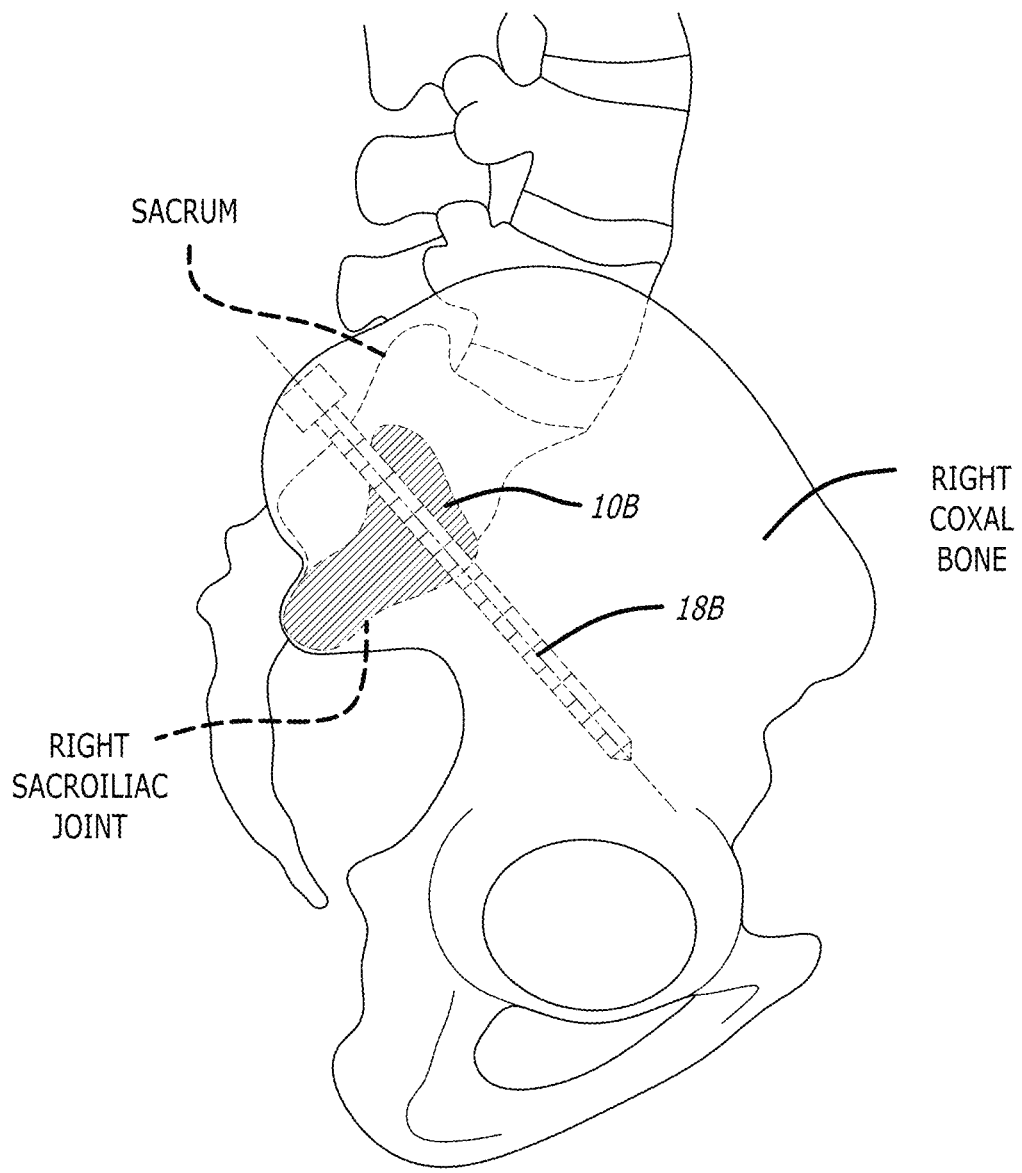
FIG. 23C is a right-side (partially phantom) representative view illustrating the right coxal bone and the sacrum showing the second bone screw and the trajectory thereof through the sacrum, the right sacroiliac joint, and the right coxal bone to facilitate stabilization of the right sacroiliac joint.

An exemplary insertion and implantation trajectory of the second bone screw 10B is depicted in FIGS. 23A-C. In FIGS. 23A-C, an aperture for receiving the second bone screw 10B can be predrilled through the right posterior portion of the sacrum, the right sacroiliac joint, and the right coxal bone, or the second bone screw can be self-drilling to form a similar aperture. The entry point for the second bone screw 10B (and the corresponding aperture therefor) depicted in FIGS. 23A and 23B would be in the third target $T_3$ of FIGS. 11 and 13. FIGS. 23B and 23C illustrate the potential length of the second bone screw 10C that traverses a large portion of the right coxal bone. As such, the insertion and implantation trajectory and length thereof serves in maximizing contact of the second bone screw 10C with cortical bone of the sacrum and the right coxal bone to increase the structured rigidity of the connection formed thereby.

Figure 14:
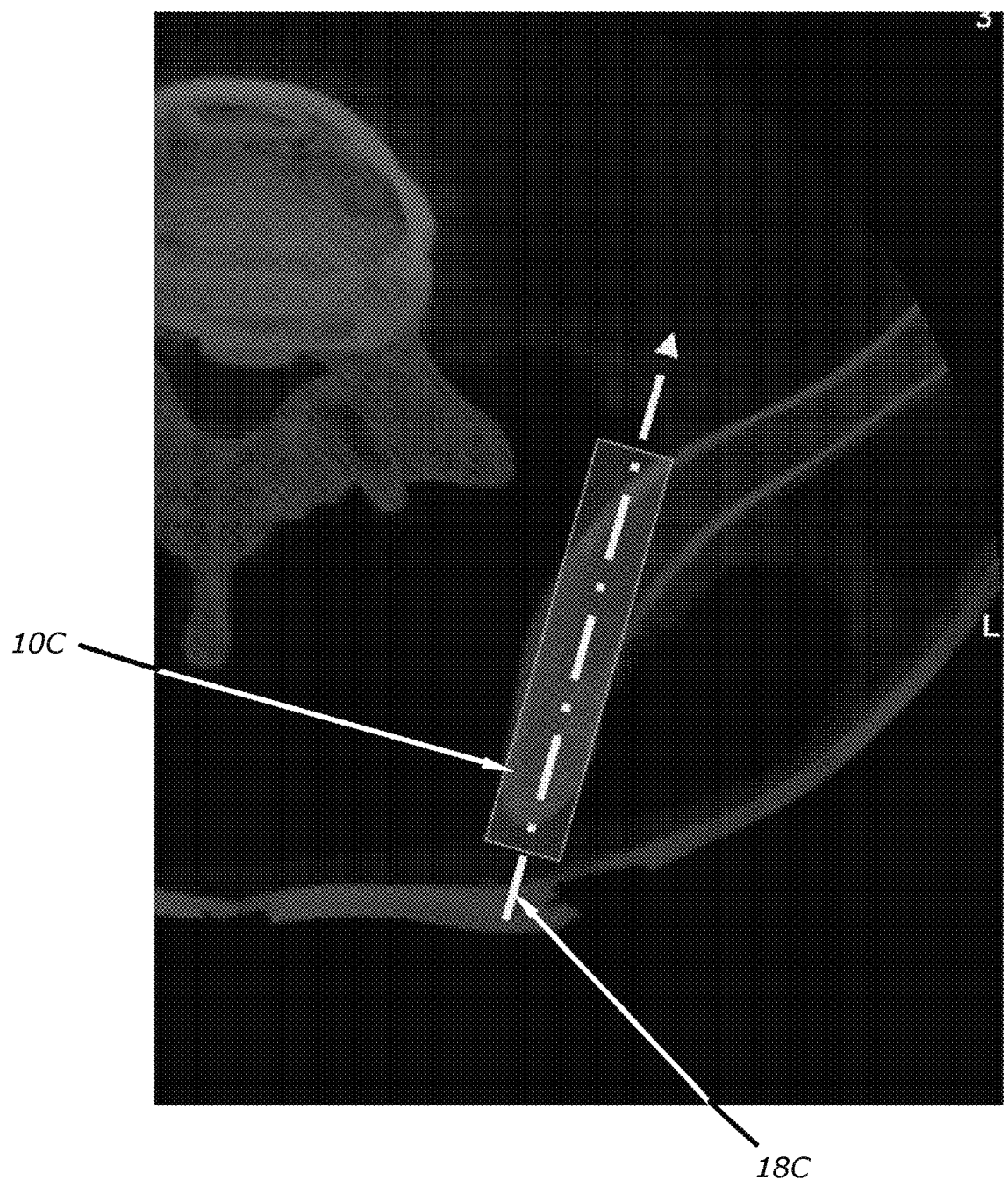
FIG. 14 is a radiographic axial cross-sectional view in a caudal direction of a portion of the pelvis of FIG. 7 showing placement of a third bone screw and an insertion direction therefor used in the surgical and the stabilization techniques according to the present disclosure to facilitate stabilization of the right sacroiliac joint.

As depicted in FIGS. 14-16, the third bone screw 10C is inserted and implanted on the right side of the patient into a second posterior portion of the posterior superior iliac spine of the iliac crest of the right coxal bone as indicated by a fifth target $T_5$ in FIG. 15, through the right coxal bone, across or at least adjacent to a portion of the right sacroiliac joint, and into the sacrum. An aperture for receiving the third bone screw 10C can be predrilled at the fifth target $T_5$ through the right coxal bone (starting at the second posterior portion of the posterior superior iliac spine), the right sacroiliac joint, and the sacrum, or the third bone screw 10C can be self-drilling to form a similar aperture. In a preferred embodiment, the third bone screw 10C can be inserted in a posterior portion of the right sacral wing, S1, or S2, and adjacent the sacral foramen positioned between S1 and S2, and serve as a S1 or S2 alar-iliac screw for fixation of the sacrum and the right coxal bone. The location of the aperture at the fifth target can be inferior to the location of the aperture at the first target $T_1$ and at an approximately similar level to the location of the third target $T_3$. After implantation, the mid-longitudinal axis 18C of the third bone screw 10C would extend through the fifth target $T_5$ of FIG. 15 located on the second posterior portion the posterior superior iliac spine of the iliac crest of the right coxal bone and through a sixth target $T_6$ of FIG. 16 located on the right anterior sacral foramen adjacent S3 and S4. Ultimately, the aperture for the third bone screw 10C and the third bone screw 10C itself traverses a 34 mm to 80 mm length portion of the right sacroiliac joint in the area 12B. A distal end of the third bone screw 10C can be approximately 24 mm to 74 mm from the surface of the right anterior sacral foramen adjacent S3 and S4. And, the predrilled aperture and/or the insertion and implantation trajectory of the third bone screw 10C is angled at approximately 60 degrees+/−7 degrees relative to an anterior side of a coronal plane extending through the center of the pelvis, angled at approximately 40 degrees+/−10 degrees relative to a cephalad side of an axial plane extending through the center of the pelvis, and angled at approximately 35 degrees+/−25 degrees relative to a right side of a sagittal plane extending through the center of the pelvis.

The insertion and implantation trajectories of the apertures for receiving the first bone screw 10A, the second bone screw 10B, and the third bone screw 10C, and the first bone screw 10A, the second bone screw 10B, and of the third bone screw 10C themselves can be preplanned before surgery using surgical planning and navigation systems that rely on radiographic images of the patient. For example, during the planning of the insertion and implantation trajectories of the bone screws 10 (or other bone anchors or fasteners), a comparison of finished insertion and implantation depths of the first bone screw 10A along the trajectory between $T_1$ and $T_2$, the second bone screw 10B along the trajectory between $T_3$ and $T_4$, and the third bone screw 10C along the trajectory $T_5$ and $T_6$ can be performed to confirm that physical interference will not occur between portions of the first bone screw 10A, the second bone screw 10B, and the third bone screw 10C. Exemplary surgical planning and navigations systems include that disclosed in U.S. Pat. No. 8,706,185. These surgical planning and navigation systems can be used in determining the best trajectories with the ranges of angles and placements identified in the present disclosure to create lattice structures of the first bone screw 10A, the second bone screw 10B, and the third bone screw 10C to facilitate stabilization of the sacroiliac joints. One or more surgical robots (that communicate with the surgical planning and navigation systems) also can be used to facilitate drilling of the apertures for the first bone screw 10A, the second bone screw 10B, and the third bone screw, and/or inserting and implanting the first bone screw 10A, the second bone screw 10B, and the third bone screw 10C. Exemplary surgical robots include that disclosed in U.S. Patent Publication No. 2023/0397956.

As discussed above, the implantation of the first bone screw 10A, the second bone screw 10B, and the third bone screw 10C serves in facilitating stabilization of one of the pelvic areas 12A and 12B across and/or adjacent the left and the right sacroiliac joints of the pelvis. As depicted in FIGS. 6A, 6B, and 18-22, the first bone screw 10A, the second bone screw 10B, and the third bone screw 10C, after implantation thereof, form a lattice structure that serves in securing the position of the left coxal bone and the left side of the sacrum relative to one another. Furthermore, as depicted in FIG. 17, the first bone screw 10A, the second bone screw 10B, and the third bone screw 10C, after implantation thereof, also form a lattice structure that serves in securing the position of the right coxal bone and the right side of the sacrum relative to one another.

Figure 24:
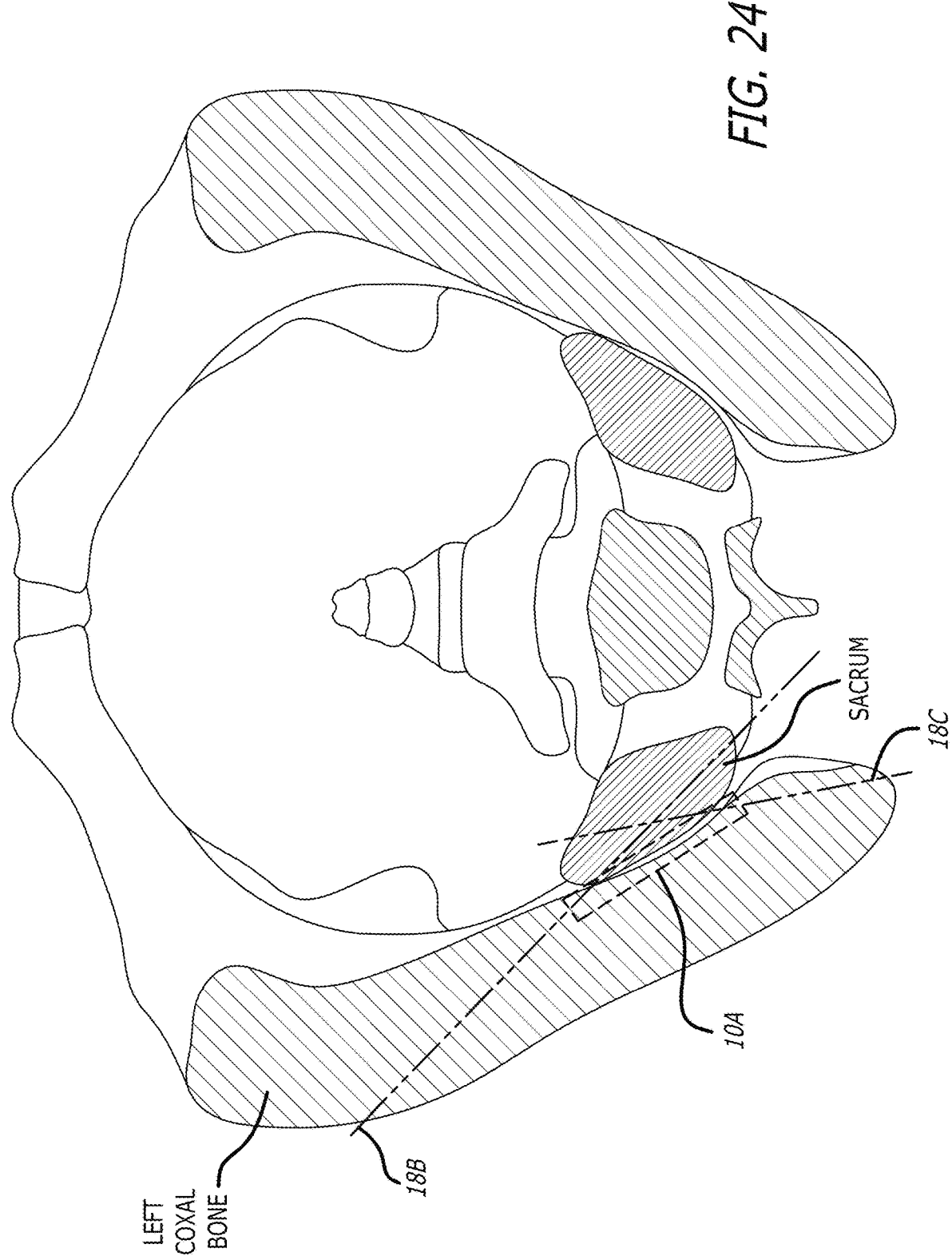
FIG. 24 is a cross-sectional representative view illustrating a cross-section of the pelvis showing the placement of the first bone screw though the right sacroiliac joint, and the axes of the second bone screw and the third bone screw passing thereby.

After insertion and implantation of the first bone screw 10A, the second bone screw 10B, and the third bone screw 10C for stabilization of the left sacroiliac joint, as depicted in FIGS. 6A, 6B, and 18-22, portions of the third bone screw 10C are positioned between portions of the first bone screw 10A and the second bone screw 10B. Furthermore, as depicted in FIGS. 6B, and 20-22, a majority of the first bone screw 10A is positioned above majorities of each of the second bone screw 10B and the third bone screw 10C. Additionally, after insertion and implantation of the first bone screw 10A, the second bone screw 10B, and the third bone screw 10C, the planes extending through the mid-longitudinal axes 18A, 18B, and 18C in cephalad-cranial directions intersect with one another. And, after insertion and implantation of the first bone screw 10A, the second bone screw 10B, and the third bone screw 10C, the first bone screw 10, as depicted in FIG. 24, can be positioned through most of the left sacroiliac joint, and the planes extending through mid-longitudinal axes 18B and 18C in the cephalad-cranial directions intersect one another medially to the sacroiliac joint and the first bone screw 10A. The positions of the first bone screw 10A, the second bone screw 10B, and the third bone screw 10C would be similar for stabilization of the right sacroiliac joint.

The lattice structure formed by the different trajectories, and corresponding different angles and placements of the first bone screw 10A, the second bone screw 10B, and the third bone screw 10C in close proximity relative to one another can create a "toe-nailing effect" increases the mechanical strength of the connection across the the left or right sacroiliac joints created thereby. To illustrate, the different angles of the first bone screw 10A, the second bone screw 10B, and the third bone screw 10C provide enhanced mechanical strength in comparison to the conventional surgical and the conventional stabilization techniques using the parallel alignment of the three (3) bone screws that can compensate for the poor strength of the sacral bone of the left and the right iliums. In doing so, the "toe-nailing effect" and the corresponding increased mechanical strength afforded by the lattice structure formed by the close proximity and different angles and placements of the first bone screw 10A, the second bone screw 10B, and the third bone screw 10C serves in resisting movement of the left or the right sacroiliac joints in a myriad of directions under the loads applied thereto. Furthermore, the packing of the first bone screw 10A, the second bone screw 10B, and/or the third bone screw 10C with the bone cement, bone graft, biodegradable polymers, or other bone-growth-promoting substances, etc. prior to insertion and implantation can afford promotion of bone ingrowth through the first bone screw 10A, the second bone screw 10B, and/or the third bone screw 10C and between the left coxal bone and the left side of the sacrum or between the right coxal bone and the right side of the sacrum to facilitate fusion of the right sacroiliac joint. In a preferred embodiment, the first bone screw 10A can be positioned, for example, through most of the left sacroiliac joint (FIG. 24) and be configured to maximize stabilization of the left sacroiliac joint and potential fusion thereof, and the second bone screw 10B and the third bones screw 10C (and the mid-longitudinal axes 18B and 18C depicted in FIG. 24) can be positioned to create the "toe-nailing effect" with one another and the first bone screw 10A to increase the mechanical properties of the corresponding connection across the sacroiliac joint. At the very least, the mechanical properties of the lattice structure of the first bone screw 10A, the second bone screw 10B, and/or the third bone screw 10C can facilitate such fusion by constraining movement of the left and the right sacroiliac joints before, during, and after such fusion is completed. By stabilizing and/or fusing the left sacroiliac iliac joint, movement can be constrained between the left coxal bone and the left side of the sacrum, and by stabilizing and/or fusing the right sacroiliac joint, movement can be constrained between the right coxal bone and the right side of the sacrum, and such constrainment can aid in the treatment of pain associated with the left and right sacroiliac joints.

Although the preferred surgical and stabilization techniques of the present disclosure describe use of a plurality of bone screws 10 (e.g., the first bone screw 10A, the second bone screw 10B, and the third bone screw 10C), other bone anchors or fasteners such as the described above can be used. These other bone anchors or fasteners can be threaded or non-threaded, be pins and/or posts with ratchets and/or teeth, and/or have cannulations and/or fenestrations therealong. Additionally, one (1) fewer or more than three (3) of such bone anchors or fasteners (including the bone screws 10) can be used. To illustrate, the first bone screw 10A, as discussed above, can be substituted with a biodegradable bag implanted in the predrilled aperture and filled with bone cement. Furthermore, two (2) bone anchors or fasteners (including the bone screws 10) can be used instead of three (3) bone anchors or fasteners provided that at least two of the above-described insertion and implantation trajectories (especially the above-described trajectories of the second bone screw 10B and the third bone screw 10C) are used. The above-described trajectories of the second bone screw 10B and the third bone screw 10C in close proximity to one another can create the "toe-nailing effect" afforded by creation of the lattice structure therebetween that provides stabilization of the sacroiliac joints. Moreover, even one (1) bone anchor or fastener (including one of the bone screws 10) inserted and implanted at the above-described trajectories (especially the above-described trajectories of the second bone screw 10B and the third bone screw 10C) can be useful in stabilization of the sacroiliac joints.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (for example, all described acts or events may not be necessary to carry out the techniques). In addition, while certain aspects of this disclosure are described as being performed by a single module or unit for purposes of clarity, it should be understood that the techniques of this disclosure may be performed by a combination of units or modules.

We claim:

1. A method for facilitating stabilization of a selected one of a right sacroiliac joint and a left sacroiliac joint of a pelvis of a patient, the method comprising:

providing an incision in one of a right portion and a left portion of a back and/or buttocks of the patient corresponding to the selected one of the right sacroiliac joint and the left sacroiliac joint;

accessing a posterior portion of one of a right coxal bone and a left coxal bone of the patient corresponding to the selected one of the right sacroiliac joint and the left sacroiliac joint;

preparing a first insertion hole through a first portion of the one of the right coxal bone and the left coxal bone, and across at least a first portion of the selected one of the right sacroiliac joint and the left sacroiliac joint between the one of the right coxal bone and the left coxal bone and one of a right side and a left side of a sacrum corresponding to the selected one of the right sacroiliac joint and the left sacroiliac joint;

preparing a second insertion hole behind a second portion of the one of the right coxal bone and the left coxal bone, through the one of the right side and the left side of the sacrum, across at least a second portion of the selected one of the right sacroiliac joint and the left sacroiliac joint, and into the one of the right coxal bone and the left coxal bone;

preparing a third insertion hole through a third portion of the one of the right coxal bone and the left coxal bone, across at least a third portion of the selected one of the right sacroiliac joint and the left sacroiliac joint, and into the one of the right side and the left side of the sacrum;

inserting a first bone anchor through and into the first insertion hole to extend through most of the selected one of the right sacroiliac joint and the left sacroiliac joint;

inserting a second bone anchor through and into the second insertion hole to extend through the one of the right side and the left side of the sacrum, across the selected one of the right sacroiliac joint and the left sacroiliac joint, and into the one of the right coxal bone and the left coxal bone to interconnect the one of the right coxal bone and the left coxal bone and the sacrum;

inserting a third bone anchor through and into the third insertion hole to extend through the one of the right coxal bone and the left coxal bone, across the selected one of the right sacroiliac joint and the left sacroiliac joint, and into the one of the right side and the left side of the sacrum to interconnect the one of the right coxal bone and the left coxal bone, and the sacrum; and forming a lattice construct by implantation of the first bone anchor, the second bone anchor, and the third bone anchor to constrain movement between the one of the right coxal bone and the left coxal bone, and the one of the right side and the left side of the sacrum to facilitate stabilization across the selected one of the right sacroiliac joint and the left sacroiliac joint;

wherein the first bone anchor, the second bone anchor, and the third bone anchor each include a first end, an opposite second end, and a mid-longitudinal axis extending through the first end and the second end, and planes extending along each of the mid-longitudinal axis in cranial-caudal directions intersect with one another within the pelvis of the patient after the implantation of the first bone anchor, the second bone anchor, and the third bone anchor; and wherein, after insertion of the first bone anchor, the second bone anchor, and the third bone anchor, the plane of the second bone anchor and the plane of the third bone anchor intersect one another on a medial side of the first bone anchor.

2. The method of claim 1, wherein, after implantation thereof, the first bone anchor is angled at approximately 83 degrees+/−7 degrees relative to a coronal plane extending through the center of the pelvis, and angled at approximately 20 degrees+/−8 degrees relative to a sagittal plane extending through the center of the pelvis.

3. The method of claim 2, wherein, after implantation thereof, the second bone anchor is angled at approximately 45 degrees+/−25 degrees relative to the coronal plane extending through the center of the pelvis, and angled at approximately 40 degrees+/−30 degrees relative to the sagittal plane extending through the center of the pelvis.

4. The method of claim 3, wherein, after implantation thereof, the third bone anchor is angled at approximately 60 degrees+/−7 degrees relative to the coronal plane extending through the center of the pelvis, and angled at approximately 35 degrees+/−25 degrees relative to the sagittal plane extending through the center of the pelvis.

5. The method of claim 4, wherein, after implantation, portions of the third bone anchor are positioned between portions of the first bone anchor and the second bone anchor.

6. The method of claim 1, wherein, after implantation, the mid-longitudinal axis of the second bone anchor extends through or adjacent a first surface located on a posterior portion of the one of the right side and the left side of the sacrum, and through or adjacent a second surface located on an ilium of the one of the right coxal bone and the left coxal bone.

7. The method of claim 6, wherein, after implantation, the mid-longitudinal axis of the third bone anchor extends through or adjacent a third surface located on a posterior portion of the posterior superior iliac spine of the iliac crest of the one of the right coxal bone and the left coxal bone, and through or adjacent a fourth surface located on an anterior sacral foramen of the sacrum.

8. The method of claim 7, wherein, after implantation, portions of the third bone anchor are positioned between portions of the first bone anchor and the second bone anchor.

9. The method of claim 1, wherein, after implantation, portions of the third bone anchor are positioned between portions of the first bone anchor and the second bone anchor.

10. The method of claim 1, further comprising packing, prior to insertion thereof, at least one of the first bone anchor, the second bone anchor, and the third bone anchor with one of bone cement, bone graft, biodegradable polymers, and other bone-growth promoting substances to promote fusion across the selected one of the right sacroiliac joint and the left sacroiliac joint.

11. The method of claim 1, wherein the plane of the first bone anchor intersects the plane of the second bone anchor adjacent a distal portion of the first bone anchor, and intersects the plane of the third bone anchor adjacent a proximal portion of the first bone anchor.

12. The method of claim 1, wherein from one of an upward view and a downward view oriented along the cranial-caudal axis, the mid-longitudinal axis of the first bone anchor intersects with the mid-longitudinal axis of the second bone anchor adjacent a distal portion of the first bone anchor, and with the mid-longitudinal axis of the third bone anchor adjacent a proximal portion of the first bone anchor.

13. The method of claim 1, wherein each of the first bone anchor and the third bone anchor include proximal end portions, and, after insertion, each of the proximal end portions of the first bone anchor and the third bone anchor contact bony surfaces of the one of the right coxal bone and the left coxal bone, and the proximal end portions of the first bone anchor and the third bone anchor are spaced apart by the bony surfaces of the one of the right coxal bone and the left coxal bone.

14. A method for facilitating stabilization of a selected one of a right sacroiliac joint and a left sacroiliac joint of a pelvis of a patient, the method comprising:

providing an incision in one of a right portion and a left portion of a back and/or buttocks of the patient corresponding to the selected one of the right sacroiliac joint and the left sacroiliac joint;

accessing a posterior portion of one of a right coxal bone and a left coxal bone of the patient corresponding to the selected one of the right sacroiliac joint and the left sacroiliac joint;

preparing a first insertion hole through a first portion of the one of the right coxal bone and the left coxal bone, and across at least a first portion of the selected one of the right sacroiliac joint and the left sacroiliac joint between the one of the right coxal bone and the left coxal bone and one of a right side and a left side of a sacrum corresponding to the selected one of the right sacroiliac joint and the left sacroiliac joint;

preparing a second insertion hole behind a second portion of the one of the right coxal bone and the left coxal bone, through the one of the right side and the left side of the sacrum, across at least a second portion of the selected one of the right sacroiliac joint and the left sacroiliac joint, and into the one of the right coxal bone and the left coxal bone;

preparing a third insertion hole through a third portion of the one of the right coxal bone and the left coxal bone, across at least a third portion of the selected one of the right sacroiliac joint and the left sacroiliac joint, and into the one of the right side and the left side of the sacrum;

inserting a first bone anchor through and into the first insertion hole to extend through most of the selected one of the right sacroiliac joint and the left sacroiliac joint;

inserting a second bone anchor through and into the second insertion hole to extend through the one of the right side and the left side of the sacrum, across the selected one of the right sacroiliac joint and the left sacroiliac joint, and into the one of the right coxal bone and the left coxal bone to interconnect the one of the right coxal bone and the left coxal bone and the sacrum;

inserting a third bone anchor through and into the third insertion hole to extend through the one of the right coxal bone and the left coxal bone, across the selected one of the right sacroiliac joint and the left sacroiliac joint, and into the one of the right side and the left side of the sacrum to interconnect the one of the right coxal bone and the left coxal bone, and the sacrum; and forming a lattice construct by implantation of the first bone anchor, the second bone anchor, and the third bone anchor to maintain the position of the one of the right coxal bone and the left coxal bone relative to the sacrum;

wherein the first bone anchor, the second bone anchor, and the third bone anchor each include a first end, an opposite second end, and a mid-longitudinal axis extending through the first end and the second end, and planes extending along each of the mid-longitudinal axis in cranial-caudal directions intersect with one another within the pelvis of the patient after the implantation of the first bone anchor, the second bone anchor, and the third bone anchor; and wherein the plane of the first bone anchor intersects the plane of the second bone anchor adjacent a distal portion of the first bone anchor, and intersects the plane of the third bone anchor adjacent a proximal portion of the first bone anchor.

15. The method of claim 14, wherein, after implantation, portions of the third bone anchor are positioned between portions of the first bone anchor and the second bone anchor.

16. The method of claim 14, wherein, after implantation, the mid-longitudinal axis of the second bone anchor extends through or adjacent a first surface located on a posterior portion of the one of the right side and the left side of the sacrum, and through or adjacent a second surface located on an ilium of the one of the right coxal bone and the left coxal bone.

17. The method of claim 16, wherein, after implantation, the mid-longitudinal axis of the third bone anchor extends through or adjacent a third surface located on a posterior portion of the posterior superior iliac spine of the iliac crest of the one of the right coxal bone and the left coxal bone, and through or adjacent a fourth surface located on an anterior sacral foramen of the sacrum.

18. The method of claim 14, wherein, after insertion of the first bone anchor, the second bone anchor, and the third bone anchor, the plane of the second bone anchor and the plane of the third bone anchor intersect one another on a medial side of the first bone anchor.

19. The method of claim 14, wherein from one of an upward view and a downward view oriented along the cranial-caudal axis, the mid-longitudinal axis of the first bone anchor intersects with the mid-longitudinal axis of the second bone anchor adjacent a distal portion of the first bone anchor, and with the mid-longitudinal axis of the third bone anchor adjacent a proximal portion of the first bone anchor.

20. The method of claim 14, wherein each of the first bone anchor and the third bone anchor include proximal end portions, and, after insertion, each of the proximal end portions of the first bone anchor and the third bone anchor contact bony surfaces of the one of the right coxal bone and the left coxal bone, and the proximal end portions of the first bone anchor and the third bone anchor are spaced apart by the bony surfaces of the one of the right coxal bone and the left coxal bone.

21. A method for facilitating stabilization of a selected one of a right sacroiliac joint and a left sacroiliac joint of a pelvis of a patient, the method comprising:

providing an incision in one of a right portion and a left portion of a back and/or buttocks of the patient corresponding to the selected one of the right sacroiliac joint and the left sacroiliac joint;

accessing a posterior portion of one of a right coxal bone and a left coxal bone of the patient corresponding to the selected one of the right sacroiliac joint and the left sacroiliac joint;

preparing a first insertion hole through a first portion of the one of the right coxal bone and the left coxal bone, and across at least a first portion of the selected one of the right sacroiliac joint and the left sacroiliac joint between the one of the right coxal bone and the left coxal bone and one of a right side and a left side of a sacrum corresponding to the selected one of the right sacroiliac joint and the left sacroiliac joint;

preparing a second insertion hole behind a second portion of the one of the right coxal bone and the left coxal bone, through the one of the right side and the left side of the sacrum, across at least a second portion of the selected one of the right sacroiliac joint and the left sacroiliac joint, and into the one of the right coxal bone and the left coxal bone;

preparing a third insertion hole through a third portion of the one of the right coxal bone and the left coxal bone, across at least a third portion of the selected one of the right sacroiliac joint and the left sacroiliac joint, and into the one of the right side and the left side of the sacrum;

inserting a first bone anchor through and into the first insertion hole to extend through most of the selected one of the right sacroiliac joint and the left sacroiliac joint;

inserting a second bone anchor through and into the second insertion hole to extend through the one of the right side and the left side of the sacrum, across the selected one of the right sacroiliac joint and the left sacroiliac joint, and into the one of the right coxal bone and the left coxal bone to interconnect the one of the right coxal bone and the left coxal bone, and the sacrum;

inserting a third bone anchor through and into the third insertion hole to extend through the one of the right coxal bone and the left coxal bone, across the selected one of the right sacroiliac joint and the left sacroiliac joint, and into the one of the right side and the left side of the sacrum to interconnect the one of the right coxal bone and the left coxal bone, and the sacrum; and forming a lattice construct by implantation of the first bone anchor, the second bone anchor, and the third bone anchor to maintain the position of the one of the right coxal bone and the left coxal bone relative to the sacrum;

wherein the first bone anchor, the second bone anchor, and the third bone anchor each include a first end, an opposite second end, and a mid-longitudinal axis extending through the first end and the second end, and planes extending along each of the mid-longitudinal axis in cranial-caudal directions;

wherein, after insertion of the first bone anchor, the second bone anchor, and the third bone anchor, the plane of the second bone anchor and the plane of the third bone anchor intersect one another on a medial side of the first bone anchor, the plane of the first bone anchor intersects the plane of the second bone anchor adjacent a distal portion of the first bone anchor, and the plane of the first bone anchor intersects the plane of the third bone anchor adjacent a proximal portion of the first bone anchor; and wherein each of the first bone anchor and the third bone anchor include proximal end portions, and, after insertion, each of the proximal end portions of the first bone anchor and the third bone anchor contact bony surfaces of the one of the right coxal bone and the left coxal bone, and the proximal end portions of the first bone anchor and the third bone anchor are spaced apart by the bony surfaces of the one of the right coxal bone and the left coxal bone.

22. The method of claim 21, wherein, after implantation, the mid-longitudinal axis of the second bone anchor extends through or adjacent a first surface located on a posterior portion of the one of the right side and the left side of the sacrum, and through or adjacent a third surface located an ilium of the one of the right coxal bone and the left coxal bone.

23. The method of claim 22, wherein, after implantation, the mid-longitudinal axis of the third bone anchor extends through or adjacent a third surface located on a posterior portion of the posterior superior iliac spine of the iliac crest of the one of the right coxal bone and the left coxal bone, and through or adjacent a fourth surface located on an anterior sacral foramen of the sacrum.

* * * * *